United States Patent
Ishii et al.

(10) Patent No.: US 6,468,487 B1
(45) Date of Patent: Oct. 22, 2002

(54) NITRATION OR CARBOXYLATION CATALYSTS

(75) Inventors: Yasutaka Ishii, Takatsuki; Tatsuya Nakano, Himeji; Satoshi Sakaguchi, Suita, all of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/142,089

(22) PCT Filed: Jan. 13, 1998

(86) PCT No.: PCT/JP98/00079

§ 371 (c)(1),
(2), (4) Date: Feb. 19, 1999

(87) PCT Pub. No.: WO98/30329

PCT Pub. Date: Jul. 16, 1998

(30) Foreign Application Priority Data

Jan. 14, 1997 (JP) .................................................. 9/4439
Feb. 17, 1997 (JP) ................................................ 9/32440
Aug. 4, 1997 (JP) .............................................. 9/209430

(51) Int. Cl.$^7$ .................................................. B01J 8/00
(52) U.S. Cl. ..................... 423/239.1; 423/235; 423/246; 423/247; 564/188; 560/141; 560/220; 568/344; 568/351
(58) Field of Search ................................. 502/150, 162; 564/188; 560/141, 220; 568/344, 351; 423/235, 239.1, 246, 247

(56) References Cited

U.S. PATENT DOCUMENTS

| | | | |
|---|---|---|---|
| 3,594,427 A | | 7/1971 | Moore |
| 3,753,950 A | | 8/1973 | Thompson |
| 3,832,332 A | | 8/1974 | Thompson |
| 5,258,507 A | * | 11/1993 | Cruickshank et al. ....... 536/24.3 |
| 5,498,695 A | * | 3/1996 | Daumy et al. ............... 530/331 |
| 5,501,952 A | * | 3/1996 | Cubbage et al. ................ 435/6 |
| 5,840,919 A | * | 11/1998 | Bronstein et al. ........... 549/220 |
| 5,955,335 A | * | 9/1999 | Thust et al. ................. 435/176 |
| 5,956,657 A | * | 9/1999 | Nakano et al. .............. 568/927 |

FOREIGN PATENT DOCUMENTS

| | | | |
|---|---|---|---|
| EP | A1 0-824962 | | 2/1998 |
| JP | B 44-12891 | | 6/1969 |
| JP | B 46-28419 | | 8/1971 |
| JP | A 50-21090 | | 3/1975 |
| JP | A 56-71075 | | 6/1981 |
| JP | A 56-92847 | | 7/1981 |
| JP | B2 7-74168 | | 8/1995 |
| JP | A 8-38909 | | 2/1996 |
| JP | A 9-143109 | | 6/1997 |
| JP | A 9-278675 | | 10/1997 |
| WO | 97/36041 | * | 10/1997 |

OTHER PUBLICATIONS

Sakaguchi, Satoshi et al., "N–Hydroxyphthalimide (NHPI)—Catalyzed Reaction of Adamantane Under Nitric Oxide Atmosphere", Tetrahedron Letters, vol. 38, No. 40, pp. 7075–7078, Oct. 6, 1997.

F. Stepanov, et al, "Adamantane and its derivatives. VIII. Synthesis and acid hydrolysis of tri–and tetra–substituted acylamino derivatives of adamantane.", Zh. Org. Khim. (1996), 2 (9), pp. 1612–1615.

Vishnevskii, E.N. et al., "Nitration of adamantane by nitrogen dioxide", Zh. Org. Khim. (1996), 32(7), pp. 1030–1035.

Richard Gilardi, et al, "Structure of 1–Amino–3,5,7–trinitroadamantane", Acta Crystallogr., Sect. C: Cryst. Struct. Commun.(1991), C47(9), pp. 1914–1916.

Zajac, Walter W. et al., "1–Amino–3,5,7–trinitroadamantane:an unexpected oxidation product of 1,3,5,7–tetraaminoadamantane. An improved synthesis of 1,3,5,7–tetranitroadamantane.", J. Org. Chem. (1989), 54(10), pp. 2468–2471.

Khil'chevskii, A.N. et al, "Reaction of adamantane and adamantane–and bicyclo [3.3.1]nonane–type carboxylic acids with acetonitrile in liquid bromine", Zh. Org. Khim. (1996), 32(7), pp. 1022–1024.

Mella, M. et al., "Oxidative Functionalization of Adamantane and Some of its Derivatives in Solution", J. Org. Chem. (1996), 61(4), pp. 1413–1422.

* cited by examiner

Primary Examiner—Steven P. Griffin
Assistant Examiner—Christina Ildebrando
(74) Attorney, Agent, or Firm—Birch, Stewart, Kolasch & Birch, LLP

(57) ABSTRACT

In the presence of an imide compound (e.g., N-hydroxyphthalimide) shown by the following formula (1):

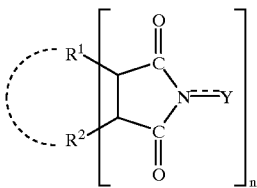

(1)

wherein $R^1$ and $R^2$ represent a hydrogen atom, a halogen atom, an alkyl group, an aryl group and a cycloalkyl group, and $R^1$ and $R^2$ may bond together to form a double bond, or an aromatic or non-aromatic ring, and Y is an O or OH, and n denotes 1 to 3; a substrate is allowed to contact with at least one reactant selected from (i) a nitrogen oxide and (ii) a mixture of carbon monoxide and oxygen to be introduced with at least one functional group selected from a nitro group and a carboxyl group. The nitrogen oxide includes, for example, a compound represented by the formula $N_xO_y$ (e.g., $N_2O_3$, $NO_2$). The substrate includes, for example, a compound having a methine carbon atom (e.g., adamantane), a compound having a methyl group or a methylene group at an adjacent moiety of an aromatic ring. According to such reaction, the substrate can be efficiently nitrated or carboxylated even in a mild or moderate condition.

13 Claims, No Drawings

US 6,468,487 B1

NITRATION OR CARBOXYLATION CATALYSTS

This application is the national phase under 35 U.S.C. §371 of prior PCT International Application No. PCT/JP98/00079 which has an International filing date of Jan. 13, 1998 which designated the United States of America, the entire contents of which are hereby incorporated by reference.

TECHNICAL FIELD

The present invention relates to a catalyst useful for directly and efficiently nitrating and/or carboxylating a substrate by using at least one reactant selected from (i) a nitrogen oxide and (ii) a mixture of carbon monoxide and oxygen, and a compound obtained by using the catalyst and a process for producing the compound (a nitration/carboxylation process, a process for producing a compound having a nitro group and/or carboxyl group, a novel adamantane derivative, and a process for producing an adamantane derivative) using the catalyst.

BACKGROUND ART

Nitro compounds are commonly utilized as a raw material for medicine, agricultural chemicals, dyes, solvents and explosives, a raw material for amino compounds, and the like. Moreover, carboxylic acids (carboxy compounds) are useful as a raw material of a variety of compounds such as esters. Among them, dicarboxylic acids are useful as a raw material of polyesters.

Nitration of hydrocarbons is generally conducted by a nitric acid process which employs a mixed acid (a mixture of nitric acid and sulfuric acid). However, the nitric acid process requires a strong acid with high concentration in a large amount. Besides, since the nitration reaction is exothermic, it is difficult to improve its reaction operability. Furthermore, in the nitric acid process, large amounts of nitrogen oxides produce, which cause environmental pollution and thus have to be treated in a proper manner.

As a nitration process, use of $N_2O_5$ and ozone in the presence of an iron catalyst has been suggested for nitration of aromatic compounds (e.g., toluene) or alicyclic compounds (e.g., adamantane). Due to the use of $NO_3$ as a reactant, this nitration process can proceed smoothly at a lower temperature. However, a catalyst should be incorporated in order to increase the reaction rate, and additional equipment such as an ozone-generating apparatus should be installed for the generation of ozone.

Carboxyl compounds (e.g., phthalic acid) can be obtained by, for example, an oxidation of a substrate (e.g., naphthalene). In Such oxidation reaction, a carboxyl compound having carbon atoms fewer than a substrate can be usually obtained. Moreover, in order to obtain a carboxyl compound of a bridged cyclic hydrocarbon (e.g., 1-carboxyladamantane) by an oxidation reaction, it is required that a group which can be converted to a carboxyl group by oxidation (e.g., methylol group) is introduced to a methine carbon atom, and then the methine carbon atom is oxidized. It is considerably difficult.

As a carboxylation process of a hydrocarbon compound, for example, a process for providing a carboxylic acid by using Grignard reaction is broadly known. In this process, many reaction steps are required since a substrate can not be directly carboxylated and include that a special compound such as an organic metal compound (e.g., a Grignard compound) is previously prepared from a substrate, carbon dioxide is allowed to act on the organic metal compound, and the organic metal compound is hydrolyzed to be carboxylated. Further, it is difficult to prepare the organic metal compound, additionally the compound is not convenient to handle.

Japanese Patent Application Laid-open No.38909/1996 (JP-A-8-38909) discloses a process which comprises contacting a substrate with oxygen to oxidize in the presence of an imide compound such as N-hydroxyphthalimide to provide a corresponding oxide (e.g., a carboxylic acid). In this process, a process for producing adipic acid from cyclohexane is described. In this process, a carboxyl compound having the same number of carbon atoms as a substrate can be obtained usually.

On the other hand, adamantane has a three-dimensionally symmetric structure and skeletons which insure mutual stabilization of each ring, and as a result, endowed with distinctive functions. Various highly functionalized copolymers can be obtained, for example, by introducing a functional group such as a carboxyl group or an amino group to adamantane and optionally deriving to other derivatives thereof. There have been proposed various production processes for obtaining such copolymers from a functional group-introduced adamantane derivative. The processes include, for example, a process of producing a polyester [e.g., Japanese Patent Application Laid-open No. 21090/1975 (JP-A-50-21090)], a process of producing a polycarbonate [e.g., U.S. Pat. No. 3,594,427], a process for producing a polyamide or a polyimide [e.g., U.S. Pat. No. 3,832,332], a process for producing a polyurethane [e.g., Japanese Patent Publication No. 12891/1969 (JP-B-44-12891)], a process for producing a polysulfone and a polysulfonate [e.g., U.S. Pat. No. 3,753,950], and a process for producing a vinyl polymer [e.g., Japanese Patent Publication No. 28419/1971 (JP-B-46-28419)].

These polymers provided from an adamantane derivative have generally excellent functions or characteristics (high functionality). They have, for example, optical characteristics such as small light-inducing loss, high refractive index, double refraction index, excellent characteristics such as moisture resistance, excellent heat resistance (heat resisting property) and thermal expansivity. Such excellent characteristics cannot be achieved with the use of conventional polymers. Accordingly, applications of said polymer have been investigated for optical materials such as optical fibers, optical elements, optical lenses, hologram, optical discs, and contact lenses, transparent resin coating compositions for organic glasses, electric conductive polymers, photosensitive materials, fluorescent materials and so forth.

On the other hand, an amino derivative derived from an alcohol of an adamantane is useful for introducing various pharmaceuticals and/or agricultural chemicals each having excellent pharmacological activity, and is used as a therapeutic agent for Parkinson's disease such as "SYMMETREL" (a trade name). A diamino body of adamantane is useful as an intermediate material for antibacterial drugs (agents) or antiviral drugs (agents).

The above mentioned diamino body (diamino form) of the adamantane is produced by aminating a dihalo body obtained by halogenating a diol body of an adamantane. However, in a process for the formation of a salt of the diamino body obtained by aminating the dihalo body of adamantane, a side reaction tends to occur, additionally it is difficult to separate and collect a free diamino body in a high yield.

It is, therefore, an object of the present invention to provide a catalyst which can efficiently nitrate and/or carboxylate a substrate, and a nitration and/or carboxylation process using the catalyst.

It is another object of the present invention to provide a catalyst which can nitrate or carboxylate a substrate by using at least one reactant selected from (i) a nitrogen oxide and (ii) a mixture of carbon monoxide and oxygen even in a mild or moderate condition, and a nitration and/or carboxylation process of a substrate using the catalyst.

A further object of the present invention is to provide a catalyst which can provide a compound having at least one functional group selected from nitro group and carboxyl group with high conversion and selectivity, and a process for producing the compound having a functional group by using the catalyst.

Another object of the present invention is to provide a process for nitration which can utilize effectively nitrogen oxides, which cause environmental pollution, for providing nitro compounds with high conversion and selectivity.

Further object of the present invention is to provide a process for producing a carboxyl compound which has more carbon atoms than the number of carbon atoms of a substrate, efficiently with simple operation at fewer steps.

Still further object of the present invention is to provide a novel adamantane derivative.

Still another object of the present invention is to provide a process which can produce a diamino body of adamantane in high yield.

DISCLOSURE OF INVENTION

The inventors of the present invention did intensive investigation to accomplish the above objects, and finally found that a reaction of at least one reactant selected from (i) a nitrogen oxide (e.g., $N_2O_3$, $N_2O$) and (ii) a mixture of carbon monoxide and oxygen with a substrate in the presence of a catalyst comprising a specific imide compound, efficiently introduce at least one functional group selected from a nitro group and a carboxyl group to the substrate and that useful adamantane derivatives including a novel adamantane derivative can be produced by using the above method.

Thus, a catalyst of the present invention is for introducing at least one functional group selected from a nitro group or a carboxyl group to a substrate by contacting the substrate with at least one reactant selected from (i) a nitrogen oxide and (ii) a mixture of carbon monoxide and oxygen to and comprises an imide compound shown by the following formula (1):

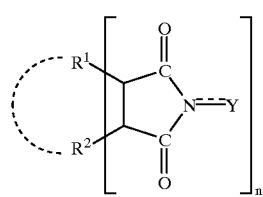

(1)

wherein $R^1$ and $R^2$ may be the same or different from each other, and represent a hydrogen atom, a halogen atom, an alkyl group, an aryl group, a cycloalkyl group, a hydroxyl group, an alkoxy group, a carboxyl group, an alkoxycarbonyl group, and an acyl group, and $R^1$ and $R^2$ may bond together to form a double bond, or an aromatic or non-aromatic ring; Y represents an oxygen atom or a hydroxyl group; and n denotes an integer of 1 to 3.

The catalyst may comprise the imide compound shown by the formula (1) and a co-catalyst. As the co-catalyst, there may be employed, for example, a compound containing at least one element selected from the group consisting of Group 2A elements of the Periodic Table of Elements, transition metal elements and Group 3B elements of the Periodic Table of Elements.

According to the process of the present invention, in the presence of the imide compound shown by the formula (1), or the imide compound and the co-catalyst, a substrate is allowed to contact with at least one reactant selected from (i) a nitrogen oxide and (ii) a mixture of carbon monoxide and oxygen to introduce at least one functional group selected from a nitro group and a carboxyl group to the substrate. The substrate includes, for example, (a) a compound having a methyl group or a methylene group at an adjacent site of an unsaturated bond, (b) a homo- or hetero cyclic compound having a methylene group, (c) a compound having a methine carbon atom, (d) a compound having a methyl group or a methylene group at an adjacent site of an aromatic ring and (e). a compound having a methylene group at an adjacent site of a carbonyl group. As the nitrogen oxide, there may be employed, for example, a compound shown by the formula:

$N_xO_y$ wherein x denotes an integer of 1 or 2 and y denotes an integer of 1 to 6;
such as $N_2O_3$, $NO_2$.

The present invention comprises a process for producing a compound having at least one functional group selected from a nitro group and a carboxyl group by using the above process, as well.

A novel adamantane derivative of the present invention is a compound shown by the following formula (2) or (3):

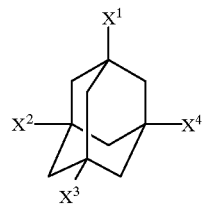

(2)

wherein $X^1$ represents a nitro group, an amino group or N-substituted amino group which may be protected by a protective group, a carboxyl group which may be protected by a protective group, or a hydroxymethyl group which may be protected by a protective group; and $X^3$ and $X^4$ may be the same or different from each other, and represents a hydrogen atom, an alkyl group, a nitro group, an amino group or N-substituted amino group which may be protected by a protective group, a carboxyl group which may be protected by a protective group, a hydroxymethyl group which may be protected by a protective group or an isocyanato group;
(i) when $X^1$ is a nitro group, $X^2$ represents an amino group or N-amino group which may be protected by a protective group, a hydroxymethyl group which may be protected by a protective group, or an isocyanato group;
(ii) when $X^1$ is an amino group or N-substituted amino group which may be protected by a protective group, $X^2$ represents an isocyanato group;
(iii) when $X^1$ is a carboxyl group which may be protected by a protective group, X represents a hydroxymethyl group which may be protected by a protective group, or an isocyanato group; and (iv) when $X^1$ is a hydroxymethyl group which may be protected by a protective group, X represents an isocyanato group;

(3)

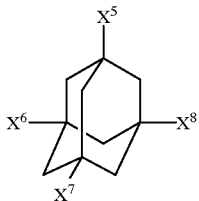

wherein $X^5$ represents a carbamoyl group which may have a substituent, a nitro group, a substituted hydoroxycarbonylamino group, or a saturated aliphatic acylamino group or an aromatic acylamino group; $X^7$ and $X^8$ are the same or different from each other, and represent a hydrogen atom, an alkyl group, a nitro group, an amino or N-substituted amino group which may be protected by a protective group, a carboxyl group which may be protected by a protective group, a hydroxymethyl group which may be protected by a protective group, or an isocyanato group;

(i) when $X^5$ is a carbamoyl group which may have a substituent, $X^6$ represents a carboxyl group, a substituted hydroxycarbonyl group, an amino group or N-substituted amino group which may be protected by a protective group, or a nitro group;

(ii) when $X^5$ is a nitro group, $X^6$ represents a substituted hydroxycarbonyl group;

(iii) when $X^5$ is a substituted hydroxycarbonylamino group, $X^6$ represents a substituted hydroxycarbonyl group, a hydroxymethyl group which may be protected by a protective group, or an amino group which may be protected by a protective group; and (iv) $X^5$ is a saturated aliphatic acylamino group or an aromatic acylamino group, $X^6$ represents a carboxyl group, a hydroxymethyl group which may be protected by a protective group, or an amino group which may be substituted by an alkyl group;

or a salt thereof.

The present invention provides a process for producing a diaminoadamantane derivative shown by the following formula (2j):

(2j)

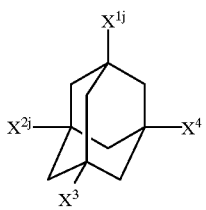

wherein $X^{1j}$ and $X^{2j}$ represent an amino group or N-substituted amino group which may be protected by a protective group; and $X^3$ and $X^4$ have the same meanings as defined above;

which comprises steps of contacting a compound shown by the following formula (2h):

(2h)

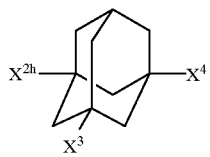

wherein $X^{2h}$ represents a hydrogen atom or a nitro group; $X^3$ and $X^4$ are have the same meanings as defined above; with a nitrogen oxide in the presence of the imide compound shown by the formula (1), to produce a dinitroadamantane derivative shown by the following formula (2i):

(2i)

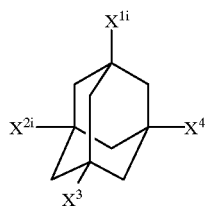

wherein $X^{1i}$ and $X^{2i}$ each represents a nitro group; and $X^3$ and $X^4$ have the same meanings as defined above; and reducing said dinitroadamantane derivative shown by the formula (2i) to produce a corresponding diamino compound.

BEST MODE FOR CARRYING OUT THE INVENTION

Imide Compound

In the compound shown by the formula (1), the halogenatom, as the substituents $R^1$ and $R^2$, includes iodine, bromine, chlorine and fluorine atoms. The alkyl group includes, for example, a straight chain or branched chain alkyl group having about 1 to 10 carbon atoms such as methyl, ethyl, propyl, isopropyl, butyl, isobutyl, sec-butyl, t-butyl, pentyl, hexyl, heptyl, octyl, and decyl group. An illustrative preferred alkyl group includes alkyl groups having about 1 to 6 carbon atoms, in particular lower alkyl groups having about 1 to 4 carbon atoms.

As the aryl group, there may be mentioned, for instance, a phenyl group and a naphthyl group. Examples of the cycloalkyl group include cyclopentyl, cyclohexyl, and cyclooctyl groups. The alkoxy group includes, for example, an alkoxy group having about 1 to 10 carbon atoms such as methoxy, ethoxy, propoxy, isopropoxy, butoxy, isobutoxy, t-butoxy, pentyloxy, andhexyloxy group. Among them, alkoxy groups having about 1 to 6 carbon atoms, in particular lower alkoxy groups having about 1 to 4 carbon atoms are preferable.

Examples of the alkoxycarbonyl group include an alkoxycarbonyl group having about 1 to 10 carbon atoms in the alkoxy moiety such as methoxycarbonyl, ethoxycarbonyl, propoxycarbonyl, isopropoxycarbonyl, butoxycarbonyl, isobutoxycarbonyl, t-butoxycarbonyl, pentyloxycarbonyl, and hexyloxycarbonyl group. A preferred alkoxycarbonyl group includes those each having about 1 to 6 carbon atoms in the alkoxy moiety, in particular lower alkoxycarbonyl groups each having about 1 to 4 carbon atoms in the alkoxy moiety.

The acyl group includes, for instance, an acyl group having about 1 to 6 carbon atoms such as formyl, acetyl, propionyl, butyryl, isobutyryl, valeryl, isovaleryl, and pivaloyl group.

The substituents $R^1$ and $R^2$ may be either the same or different from each other. In the formula (1), $R^1$ and $R^2$ may bond together to form a double bond, or an aromatic or non-aromatic ring. A preferred aromatic or non-aromatic ring may be a ring having about 5 to 12 members, in particular about 6 to 10 members. Such a ring may be a heterocyclic ring or a condensed heterocyclic ring, and it may practically be a hydrocarbon ring. As such a ring, there may be mentioned, for instance, non-aromatic alicyclic rings (e.g., cycloalkane rings which may have a substituent, such as cyclohexane ring, and a cycloalkene rings which may have a substituent, such as a cyclohexene ring), non-aromatic bridged (cross-linked) rings (e.g., bridged hydrocarbon rings which may have a substituent, such as a 5-norbornene ring), aromatic rings which may have a substituent, such as a benzene ring, a naphthalene ring. The ring may practically comprise an aromatic ring.

A preferred imide compound includes compounds shown by the following formula:

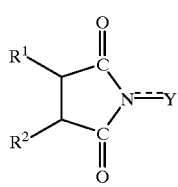
(1a)

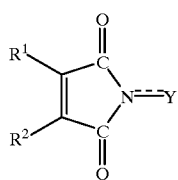
(1b)

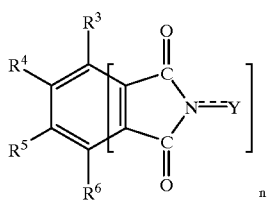
(1c)

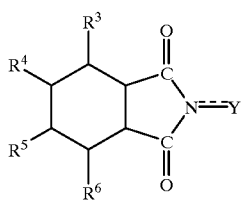
(1d)

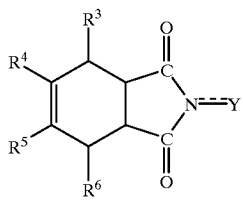
(1e)

-continued

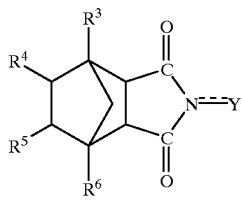
(1f)

where $R^3$, $R^4$ and $R^6$ independently represent a hydrogen atom, an alkyl group, a hydroxyl group, an alkoxy group, a carboxyl group, an alkoxycarbonyl group, an acyl group, a nitro group, a cyano group, an amino group or a halogen atom; and $R^1$, $R^2$, Y and n have the same meanings as defined above.

In the substituents $R^3$, $R^4$, $R^5$ and $R^6$, the alkyl group includes alkyl groups similar to those exemplified above, in particular alkyl groups each having about 1 to 6 carbon atoms. The alkoxy group includes the same alkoxy groups as mentioned above, in particular lower alkoxy groups each having about 1 to 4 carbon atoms. Examples of the alkoxycarbonyl group include the same alkoxycarbonyl groups as exemplified above, in especial lower alkoxycarbonyl groups each having about 1 to 4 carbon atoms in the alkoxy moiety. As the acyl group, there may be mentioned the similar acyl groups to those mentioned above, in particular acyl groups each having about 1 to 6 carbon atoms. Examples of the halogen atom include fluorine, chlorine and bromine atoms. The substituents $R^3$, $R^4$, $R^5$ and $R^6$ may practically be hydrogen atoms, lower alkyl groups each having 1 to 4 carbon atoms, carboxyl groups, nitro groups or halogen atoms, respectively.

The symbol Y in the formula (1) denotes an oxygen atom or a hydroxyl group, and n usually denotes about 1 to 3, preferably 1 or 2. The compound shown by the formula (1) can be used singly or in combination of two or more in the nitration reaction.

As examples of the acid anhydride corresponding to the imide compound of the formula (1), there may be mentioned a saturated or unsaturated aliphatic dicarboxylic acid anhydride such as succinic anhydride, maleic anhydride; a saturated or unsaturated nonaromatic cyclic polycarboxylic acid anhydride (an alicyclic polycarboxylic acid anhydride) such as tetrahydrophthalic anhydride, hexahydrophthalic anhydride (1,2-cyclohexanedicarboxylic acid anhydride), 1,2,3,4-cyclohexanetetracarboxylic acid 1,2-anhydride; a bridged cyclic polycarboxylic acid anhydride (an alicyclic polycarboxylic acid anhydride) such as hetic anhydride, himic anhydride; an aromatic polycarboxylic acid anhydride such as phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic acid dianhydride.

Examples of a preferred imide compound include N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide, N,N-dihydroxynaphthalenetetracarboximide and so forth. A typically preferable imide compound includes an N-hydroxyimide compound derived from an alicyclic polycarboxylic acid anhydride, in particular from an aromatic polycarboxylic acid anhydride, such as N-hydroxyphthalimide.

The imide compound may be prepared by a conventional imidation process (a process for the formation of an imide), such as a process that comprises the steps of allowing a corresponding acid anhydride to react with hydroxylamine $NH_2OH$ for ring-opening. of an acid anhydride group, and closing the ring to form the imide.

[Co-catalyst]

A catalyst may comprise the imide compounds of the formula (1) and a co-catalyst. The co-catalyst includes or comprises metal compounds such as a compound comprising or containing a Group 2A element of the Periodic Table of Elements (e.g., magnesium, calcium, strontium, barium), a transition metal compound, or compounds containing a Group 3B element (e.g., boron B, aluminium Al) of the Periodic Table of Elements. These co-catalysts may be employed independently or in combination of two or more.

As the elements of the transition metal, there may be mentioned, for instance, Group 3A elements of the Periodic Table of Elements (e.g., scandium Sc, yttrium Y, and a lanthanoid element such as lanthanum La, cerium Ce, samarium Sm, an actinoid element such as actinium Ac), Group 4A elements of the Periodic Table of Elements (e.g., titanium Ti, zirconium Zr, hafnium Hf), Group 5A elements (e.g., vanadium V, niobium Nb, tantalum Ta), Group 6A elements (e.g., chromium Cr, molybdenum Mo, tungsten W), Group 7A elements (e.g., manganese Mn, technetium Tc, rhenium Re), Group 8 elements (e.g., iron Fe, ruthenium Ru, osmium Os, cobalt Co, rhodium Rh, iridium Ir, nickel Ni, palladium Pd, platinum Pt), Group 1B elements (e.g., copper Cu, silver Ag, gold Au) and Group 2B elements (e.g., zinc Zn, cadmium Cd) of the Periodic Table of Elements.

A preferred element constituting the co-catalyst includes elements of the transition metals, for example, Group 3A elements of the Periodic Table of Elements such as lanthanoid elements (e.g., Ce), actinoid elements; Group 4A elements such as Ti, Zr; Group 5A elements such as V, Nb; Group 6A elements such as Cr, Mo, W; Group 7A elements such as Mn, Tc, Re; Group 8 elements such as Fe, Ru, Co, Rh, Ni; or Group 1B elements such as Cu) and Group 3B elements such as B. The oxidation number of the metal elements constituting the co-catalyst is not particularly limited, and may be, for example 0, +2, +3, +4, +5 and +6 according to the variety of elements. The divalent transition metal compounds (such as a divalent cobalt compound, a divalent manganese compound) may be practically used as the co-catalyst.

The co-catalyst may be a simple substance or hydroxide of a metal. The co-catalyst may practically be an a metal oxide (comprising a double oxide or an oxygen acid or a salt thereof) comprising the element, an organic acid salt comprising the element, an inorganic acid salt comprising the element, a halide comprising the element, a coordinate compound (a complex) comprising the metal element, or a polyacid (a heteropolyacid or an isopolyacid) comprising the element or a salt thereof.

As the boron compound, there may be mentioned, for example, a boron hydride (e.g., borane, diborane, tetraborane, pentaborane, decaborane); aboric acid (e.g., orthoboric acid, metaboric acid, tetraboric acid); a borate (e.g., a nickel borate, magnesium borate, manganese borate); boron oxides such as $B_2O_3$; nitrogen-containing boron compounds such as borazane, borazene, borazine, boron amide, boron imide; halides such as $BF_3$, $BCl_3$, tetrafluoroborate; esters of boric acid (e.g., methyl borate, phenyl borate). A preferred boron compound includes boron hydrides and boric acids such as orthoboric acid or salts thereof, in particular a boric acid.

The hydroxide includes $Mn(OH)_2$, $MnO(OH)$, $Fe(OH)_2$ and $Fe(OH)_3$, typically speaking. Examples of the metallic oxide include $Sm_2O_3$, $TiO_2$, $ZrO_2$, $V_2O_3$, $V_2O_5$, $CrO$, $Cr_2O_3$, $MoO_3MnO$, $Mn_3O_4$, $Mn_2O_3$, $Mno_2$, $Mn_2O_7$, $FeO$, $Fe_2O_3$, $Fe_3O_4$, $RuO_2$, $RuO_4$, $CoO$, $CoO_2$, $Co_2O_3$, $RhO_2$, $Rh_2O_3$, $Cu_2O_3$. As examples of the double oxide or oxygen acid salt, there may be mentioned $MnAl_2O_4$, $MnTiO_3$, $LaMnO_3$, $K_2Mn_2O_5$, $CaO.xMnO_2$ (x=0.5, 1, 2, 3, 5), manganese salts [e.g., manganates (V) such as $Na_3MnO_4$, $Ba_3(MnO_4)_2$; manganates(VI) such as $K_2MnO_4$, $Na_2MnO_4$, $BaMnO_4$; permanganates such as $KMnO_4$, $NaMnO_4$, $LinO_4$, $NH_4MnO_4$, $CsMnO_4$, $AgMnO_4$, $Ca(MnO_4)_2$, $Zn(Mno_4)_2$, $Ba(MnO_4)_2$, $Mg(MnO_4)_3$, $Cd(MnO_4)_2$].

As the organic acid salts, there may be exemplified as salts of a $C_{2-20}$ fatty acid such as cobalt acetate, manganese acetate, cobalt propionate, manganese propionate, cobalt naphthenate, manganese naphthenate, cobalt stearate and manganese stearate, and manganese thiocyanate and corresponding salts of Ce, Ti, Zr, V, Cr, Mo, Fe, Ru, Ni, Pd, Cu and Zn. The inorganic acid salt includes, for instance, nitrates such as cobalt nitrate, iron nitrate, manganese nitrate, nickel nitrate and copper nitrate, and sulfates, phosphates and carbonates each corresponding to these nitrates (e.g., cobalt sulfate, iron sulfate, manganese sulfate, cobalt phosphate, iron phosphate, manganese phosphate, an iron carbonate, a manganese carbonate, iron perchlorate). As the halides, there may be mentioned, for instance, chlorides such as $SmCl_3$, $SmCl_2$, $TiCl_2$, $ZrCl_2$ $ZrOCl_2$, $VCl_3$, $VOCl_2$, $MnCl_2$, $MnCl_3$, $FeCl_2$, $FeCl_3$, $RuCl_3$, $CoCl_3$, $RhCl_2$, $RhCl_3$, $NiCl_2$, $PdCl_2$, $PtCl_2$, $CuCl$ and $CuCl_2$, or halides such as fluorides, bromides or iodides each corresponding to these chlorides (e.g., $MnF_2$, $MnBr_2$, $MnF_3$, $FeF_2$, $FeF_3$, $FeBr_2$, $FeBr_3$, $FeI_2CuBr$, $CuBr_2$), complex halides such as $M^1MnCl_3$, $M^1_2MnCl_4$, $M^1_2MnCl_5$, $M^1_2MnCl_6$, wherein $M^1$ represents a monovalent metal.

The ligand constituting the complex includes, for example, OH (hydroxo); alkoxy groups such as methoxy, ethoxy, propoxy and butoxy group; acyl groups such as acetyl (OAc), propionyl group; alkoxycarbonyl groups such as methoxycarbonyl (acetato), ethoxycarbonyl group; acetylacetonato (AA), cyclopentadienyl group; halogen atoms such as chlorine, bromine; CO, CN, oxygen atom, $H_2O$ (aquo); phosphorus compounds such as a phosphine (e.g., triphenylphosphine and other triarylphosphine); nitrogen-containing compounds such as $NH_3$ (ammine), NO, $NO_2$ (nitro), $NO_3$ (nitrato), ethylenediamine, diethylenetriamine, pyridine and phenanthroline. In the complexes or complex salts, the same or different ligands may be coordinated singly or in combination of two or more. The preferable ligand includes, for example, OH, an alkoxy group, an acyl group, an alkoxycarbonyl group, acetylacetonato, a halogen atom, CO, CN, $H_2O$ (aquo), triphenylphosphine and other phosphorus compounds, and a nitrogen-containing compound inclusive of $NH_3$, $NO_2$ and $NO_3$.

A preferable complex includes the complexes containing the preferable transition metal element. The transition metal element and the ligand may optionally be employed in combination to form a complex. Such a complex includes, for instance, acetylacetonato complexes [e.g., acetylacetonato complex of Ce, Sm, Ti, Zr, V, Cr, Mo, Mn, Fe, Ru, Co, Ni, Cu and Zn, titanylacetylacetonato complex $TiO(AA)_2$, zirconylacetylacetonato complex $ZrO(AA)_2$, vanadylacetylacetonato complex $VO(AA)_2$], cyano complexes [e.g., a hexacyanomanganate(I), a hexacyanoferrate(II)], carbonyl complexes or cyclopentadienyl complexes [e.g., tricarbonylcyclopentadienylmanganese(I), biscyclopentadienylmanganese(II), biscyclopentadienyliron (II), Fe(CO)$_5$, Fe$_2$(CO)$_9$, Fe$_3$(CO)$_{12}$], nitrosyl compounds [e.g., Fe(NO)$_4$, Fe(CO)$_2$(NO)$_2$], thiocyanato complexes [e.g., thiocyanatocobalt, thiocyanatomanganese, thiocyanatoiron], or acetyl complexes [e.g. cobalt acetate, manganese acetate, iron acetate, copper acetate, zirconyl acetate ZrO(OAc)$_2$, titanyl acetate TiO(OAc)$_2$, vanadyl acetate VO(OAc)$_2$].

The polyacid is practically at least one member selected from Group 5 elements or Group 6 elements of the Periodic Table of Elements, such as V (vanadic acid), Mo (molybdic acid) and W (tungstic acid), typically speaking. There is no particular limit as to the central atom, and it may be any of, for instance, Be, B, Al, Si, Ge, Sn, Ti, Zr, Th, N, P, As, Sb, V, Nb, Ta, Cr, Mo, W, S, Se, Te, Mn, I, Fe, Co, Ni, Rh, Os, Ir, Pt or Cu. As illustrative examples of the heteropolyacid, there may be mentioned cobaltmolybdic acid, cobalttungstic acid, molybdenumtungstic acid, manganesemolybdic acid, manganesetungstic acid, manganesemolybdenumtungstic acid, vanadomolybdophosphoric acid, manganesevanadiummolybdic acid, manganesevanadomolybdophosphoric acid, vanadiummolybdic acid, vanadiumtungstic acid, silicomo-lybdic acid, silicotungstic acid, phosphomolybdic acid, phosphotangstic acid, phosphovanadomolybdic acid, and phosphovanadotangstic acid.

The catalysts have high activities. A combination of the catalyst with at least one reactant selected from (i) a nitrogen oxide and (ii) a mixture of carbon monoxide and oxygen, accelerates a nitration and/or carboxylation reaction of a substrate even in a mild or moderate condition.

A catalyst comprising the imide compound shown by the formula (1) or the imide compound and the above co-catalyst may be whichever of a homogeneous system or a heterogeneous system. The catalyst may be a solid catalyst comprising a catalytic component supported on a support or carrier, as well. As the support, use can be practically made of porous supports such as active carbon, zeolite, silica, silica-alumina, and bentonite. In the solid catalyst, the supporting amount of the imide compound of the formula (1) as the catalyst component may be about 0.1 to 50 parts by weight, preferably about 0.5 to 30 parts by weight and more preferably about 1 to 20 parts by weight relative to 100 parts by weight of the support. The supporting amount more of the co-catalyst is about 0.1 to 30 parts by weight, preferably about 0.5 to 25 parts by weight, and more preferably about 1 to 20 parts by weight, relative to 100 parts by weight of the support.

Nitrogen Oxide

The nitrogen oxide may be shown by the formula:

$N_xO_y$ wherein x denotes an integer of 1 or 2 and y denotes an integer of 1 to 6.

In the compound shown by the above formula, when x is 1, y is usually an integer of 1 to 3; and when x is 2, y is usually an integer of 1 to 6.

Such nitrogen oxide may be exemplified N$_2$O, NO, N$_2$O$_3$, NO$_2$, N$_2$O$_4$, N$_2$O$_5$, NO$_3$ and N$_2$O$_6$. These nitrogen oxides may be used independently or in combination.

The preferred nitrogen oxide includes (i) a nitrogen oxide (particularly N$_2$O$_3$) generated by the reaction of at least one nitrogen oxide selected from dinitrogen oxide (N$_2$O) and nitrogen monoxide (NO) with oxygen, or a nitrogen oxide containing N$_2$O$_3$ as a main component and (ii) a nitrogen dioxide (NO$_2$) or a nitrogen oxide containing NO$_2$ as a main component.

Nitrogen oxide N$_2$O$_3$ may be easily obtained by a reaction of N$_2$O and/or NO with oxygen. To be more concrete, the nitrogen oxide may be prepared by introducing nitrogen monoxide and oxygen to a reactor to produce a blue liquid N$_2$O$_3$. Therefore, the nitration reaction may be carried out by introducing N$_2$O and/or NO and oxygen to a reaction system without producing N$_2$O$_3$ in advance.

Incidentally, a pure oxygen may be used or may be distilled by an inert gas (e.g., carbon dioxide, nitrogen, helium and argon). Air may be used as an oxygen source.

Mixture of Carbon Monoxide and Oxygen

Carbon monoxide or oxygen employed in the present invention may be pure one, and may be diluted with a inert gas (e.g., nitrogen, helium, argon, carbon dioxide). The oxygen source may be air. To the reaction system, a mixture previously mixed carbon monoxide with oxygen may be introduced, and carbon monoxide and oxygen may separately introduced.

In the present invention, as a reactant, there may be employed, for example, (i) the nitrogen oxide, (ii) the mixture of carbon monoxide and oxygen, or a combination of (i) the nitrogen oxide and (ii) the mixture of carbon monoxide and oxygen. In the case of using (i) the nitrogen oxide as a reactant, a substrate is nitrated to generate a nitro compound. In the case of using (ii) the mixture of the nitrogen monoxide and oxygen as the reactant, a substrate is carboxylated to generate a carboxyl compound. In the case of using (i) the nitrogen monoxide and (ii) the mixture of carbon monoxide and oxygen in combination as the reactant, a nitro compound and a carboxyl compound can be co-produced. In this case, use of a compound having plural reactive sites as a substrate can provide a compound which has a nitro group and a carboxyl group in the same molecule in one step by selecting a reaction condition (e.g., the ratio of the reactant (i) to (ii), a reaction temperature).

Substrate

Species of substrates is not particularly restricted, and may be employed broad range of a saturated or unsaturated compound such as a hydrocarbon (e.g., an aliphatic hydrocarbon, an alicyclic hydrocarbon, an aromatic hydrocarbon), a heterocyclic compound, an alcohol, an ether, a ketone, an aldehyde, a carboxylic acid or derivative thereof, and the like may be employed.

Preferred substrate comprises, for example, (a) a compound having a methyl group or a methylene group at the adjacent site of an unsaturated bond, (b) a homo- or heterocyclic compound having a methylene group, (c) a compound having a methine carbon atom, (d) a compound having a methyl group or a methylene group at the adjacent site of an aromatic ring and (e) a compound having a methyl group or a methylene group at the adjacent site of a carbonyl group. In the compound (b), the methylene group constitutes a 5- or 6-membered ring, and the compound (b) is usually a non-aromatic homo- or heterocyclic compound.

(a) The compound having a methyl group or a methylene group at the adjacent site of an unsaturated bond comprises an organic compound having a double bond and/or a triple bond. Examples of such compounds include propylene, 1-butene, 2-butene, butadiene, 1-pentene, 2-pentene, isoprene, 2-methyl-2-butene, 1-hexene, 2-hexene, 1,5-hexadiene, 2,3-dimethyl-2-butene, 3-hexene, 1-heptene, 2-heptene, 1,6-heptadiene, 1-octene, 2-octene, 3-octene, 1,7-octadiene, 2,6-octadiene, 1-nonene, 2-nonene, decene, decadiene, dodecadiene, dodecatriene, undecene, undecadiene and undecatriene.

(b) Examples of the homocyclic compound (b1) having methylene group include a cycloalkane (e.g., a cycloalkane having about 3 to 30 carbon atoms such as cyclopropane, cyclobutane, cyclopentane, cyclohexane, cycloheptane, methylcyclohexane, cyclooctane, 1,2-dimethylcyclohexane, cyclononane, isopropylcyclohexane, methylcyclooctane, cyclodecane, cyclododecane, cyclotridecane, cyclotetradecane, cyclopentadecane, cyclohexadecane, cyclooctadecane, cyclononadecane), a cycloalkene (e.g., a cycloalkene having about 3 to 30 carbon atoms such as cyclopropene, cyclobutene, cyclopentene, cyclohexene, cycloheptene, 1-methyl-1-cyclohexene, cyclooctene, cyclononene, cyclodecene, cyclododecene, limonene, menthene, menthone), a cycloalkadiene (e.g., a cycloalkadiene having about 5 to 30 carbon atoms such as cyclopentadiene, cyclohexadiene, cycloheptadiene, cyclooctadiene, cyclodecadiene, cyclododecadiene), a cycloalkatriene (e.g., cyclooctatriene), cycloalkatetraene (e.g., cyclooctatetraene) and a condensed polycyclic hydrocarbon.

(b) The heterocyclic compound (b2) having a methylene group comprises a 5- or 6-membered cyclic compound having at least one hetero atom selected from nitrogen atom, oxygen atom and sulfur atom, or a condensed heterocyclic compound which is condensed by the 5- or 6-membered cyclic compound having the hetero atom at an aromatic ring, such as dihydrofuran, tetrahydrofuran, pyran, dihydropyran, tetrahydropyran, piperidine, piperadine, pyrrolidine, xanthene, and the like.

(c) The compound having a methine carbon atom (methylidine group) comprises, for instance, a chain hydrocarbon (c1) having a tertiary carbon atom, a bridged cyclic hydrocarbon (c2) and the like.

Examples of the chain hydrocarbon (c1) having a tertiary carbon atom include a aliphatic hydrocarbon having about 4 to 10 carbon atoms such as isobutane, isopentane, isohexane, 3-methylpentane, 2,3-dimethylbutane, 2-methylhexane, 3-methylhexane, 2,3-dimethylpentane, 2,4-dimethylpentane, 2,3,4-trimethylpentane, 3-ethylpentane, 2,3-dimethylhexane, 2,4-dimethylhexane, 3,4-dimethylhexane, 2,5-dimethylhexane, 2-propylhexane, 2-methylheptane, 4-methylheptane, 2-ethylheptane, 3-ethylheptane, 2,6-dimethylheptane, 2-methyloctane, 3-methyloctane, 2,7-dimethyloctane and 2-methylnonane.

The bridged cyclic hydrocarbon (c2) comprises, for example, a bridged cyclic hydrocarbon [e.g., bicyclo hydrocarbon such as decalin, hexahydroindan, carane, bornane, norbornene, norbornane, vinylnorbornene and norbornadiene; a tricyclo hydrocarbon such as homoblendane, adamantane and derivatives thereof (e.g., methyladamantane, 1,3-dimethyladamantane, ethyladamantane, chloroadamantane, adamantanol, adamantanone, methyladamantanone, dimethyladamantanone, formyladamantanone), tricyclo[4.3.1.1$^{2,5}$]undecane; and a tetracyclohydorocarbon such as tetracyclo[4.4.0.1.$^{2,5}$.1.$^{7,10}$] dodecane], a dimer of a diene or hydrogen adduct thereof (e.g., dicyclopentane, dicyclohxane, dicyclopentene, dicyclohexadiene, dicyclopentadiene, tetrahydrodicyclopentadiene) and a terpene (e.g., pinane, pinene, camphor, bornene, caryophyllene).

The preferred compound (c) having a methine carbon atom includes a bridged cyclic hydrocarbon having about 6 to 16 carbon atoms, in particular about 7 to 14 (especially a bridged cyclic hydrocarbon such as adamantane or a derivative thereof).

(d) Examples of the compound having a methyl group or a methylene group at the adjacent site of an aromatic ring include an aromatic hydrocarbon having an alkyl group (e.g., toluene, o-, m- or p-xylene, 1,2,3-trimethylbenzene, 1,2,4-trimethylbenzene, 1,3,5-trimethylbenzene (mesitylene), 1,2,3,4-tetramethylbenzene, 1,2,3,5-tetramethylbenzene, 1,2,4,5-tetramethylbenzene (durene), 1,2,3,4,5,6-hexamethylbenzene, ethylbenzene, propylbenzene, cumene, o-, m- or p-ethyltoluene, butylbenzene, 1,4-diethylbenzene, 1-methylnaphthalene, 2-methylnaphthalene, 1,5-dimethylnaphthalene, 2,5-dimethylnaphthalene, 1-methylanthracene, 2-methylanthracene, 9-methylanthracene, dimethylanthracene, trimethylanthracene, 4,4'-dimethylbiphenyl, dibenzyl, diphenylmethane, triphenylmethane), an aromatic hydrocarbon having a cyclic methylene group (e.g., a condensed polycyclic aromatic hydrocarbon condesed by a about 5 to 8 -membered ring, such as indane, indene, tetralin, dihydronaohthalene, fluorene, phenalene) and a heterocyclic compound having an alkyl group (e.g., a picoline such as 2-methylfuran, 3-methylfuran, 2-methylpyran, 3-methylpyran, 4-methylpyran, 3,4-dimethylpyran, 4-methylchroman, 6-methylchroman, 2-methylpyridine, 3-methylpyridine and 4-methylpyridine, a lutidine such as 2,3-dimethyipyridine, a collidine such as 2,4,6-trimethylpyridine, 2-ethylpyridine, 3-ethylpyridine, 4-ethylpyridine, methylquinoline and methylindole). The preferred compound (d) includes a compound having a methyl group or a methylene group at benzyl position.

(e) The compound having a (active) methyl group or methylene group at the adjacent site of a carbonyl group comprises, for instance, an aldehyde (e1), a ketone (e2) and a carboxylic acid or derivative thereof (e3).

The aldehyde (e1) comprises, for example, an aliphatic aldehyde (e.g., an aliphatic monoaldehyde having about 2 to 12 carbon atoms such as acetaldehyde, propionaldehyde, butylaldehyde, isobutylaldehyde, pentylaldehyde, hexylaldehyde, heptylaldehyde, octylaldehyde, nonylaldehyde and decylaldehyde, an aliphatic polyaldehyde such as malonaldehyde, succinaldehyde, adipic aldehyde and sebacic aldehyde), an aromatic aldehyde (e.g., benzaldehyde, anisaldehyde), an alicyclic aldehyde (e.g., formylcyclohexane, citronellal), a bridged cyclic aldehyde (e.g., formylnorbornene) and a heterocyclic aldehyde (e.g., nicotinic aldehyde, furfural).

Examples of the ketone (e2) include an aliphatic ketone (e.g., acetone, methylethylketone, methylisopropylketone, methylisobutylketone, methyl-t-butylketone, 2-pentanone, 3-pentanone, 2-hexanone, 3-hexanone, 2-heptanone, 3-heptanone, 4-heptanone, 2-octanone, 3-octanone, 4-octanone, 2-nonanone and 2-decanone), a cyclic ketone (e.g., a non-aromatic cyclic mono- or polyketone such as cyclopentanone, cyclohexanone, methylcyclohexanone, dimethylcyclohexanone, cycloheptanone, isophorone, cyclooctanone, cyclononanone, cyclodecanone, cyclohexadione and cyclooctadione; a cyclic ketone having an aromatic ring such as α-tetralone, β-tetralone and indanone), a bridged cyclic ketone (e.g., pinocamphone, pinocarbon), an aromatic ketone (e.g., acetophenene, propiophenone) and a heterocyclic ketone (e.g., pyrrolidone, pyperidone).

The carboxylic acid or derivatives thereof (e3) comprises, for. example, an aliphatic dicarboxylic acid or dericatives thereof (e.g., malonic acid or an ester thereof, succinic acid or an ester thereof and glutaric acid or an ester thereof).

These substrates may be substituted by a suitable functional group, such as a halogen atom, an oxo group, a hydroxyl group, an alkoxy group, a carboxyl group, an alkoxycarbonyl group, an acyl group, an alkyl group, an alkenyl group (e.g., an allyl group), a cycloalkyl group, an aryl group, a vinyl group, an amino group, an alkylamino group, an amido group, a nitro group, a nitrile group, an acylamino group, a mercapto group, a sulfonyl group, a sulfinyl group, a sulfide group and a phosphino group.

In such substrates (a), (b), (c), (d) and (e), a nitro group or a carboxyl group can be introduced thereto at a carbon atom of a methyl or methylene group, or a methine carbon atom. To be specific, a nitro group or a carboxyl group can be smoothly introduced to the compound (c) at a methine carbon atom such as a cyclic methine carbon atom of the bridged cyclic hydrocarbon to provide a nitro compound or a carboxy compound of the bridged cyclic hydrocarbonwithhighconversionandselectivity. Contact of, for example, adamantane among the bridged cyclic hydrocarbons with the nitrogen oxide in the presence of the catalyst provides 1-nitroadamantane and/or 1,3-dinitroadamantane and/or 1,3, 5-trinitroadamantane etc. Contact of adamantane with carbon monoxide and oxygen provides 1-carboxyadamantane and/or 1,3-dicarboxyadamantane and/or 1,3,5-tricarboxyadamantane etc. Moreover, contact of adamantane with the nitrogen oxide, carbon monoxide and oxygen in the presence of the catalyst provides 1-carboxy-3-nitroadamantane, 1-carboxy-3,5-dinitroadamantane, 1,3-dicarboxy-5-nitroadamantane etc. Furthermore, contact of 1-methyladamantane with the nitrogen oxide provides 1-methyl-3-nitroadamantane, contact of 1-methyladamantane with carbon monoxide and oxygen provides 1-carboxy-3-methyladamantane etc.

In (d) the compound having a methyl group or a methylene group at an adjacent site of an aromatic ring, a nitro group or a carboxyl group can be smoothly introduced thereto at the benzyl position. Contact of, for example, toluene among the compound having a methyl group or a methylene group at the benzyl position with the nitrogen oxide in the presence of the catalyst provides nitrobenzene etc. and contact of toluene with the carbon monoxide and oxygen provides phenylacetate. Use of ethylbenzene as a substrate provides 1-nitroethylbenzene, 1-phenylpropionate etc. Application of the process of the present invention to fluorene provides 9-carboxyfluorene.

Amount and Ratio of the Each Component

The amount of the imide compound shown by the formula (1) may be selected within a broad range, for example, of about 0.0001 mole (0.01 mole %) to 1 mole (100 mole %), preferably about 0.001 mole (0.1 mole %) to 0.5 mole (50 mole %), more preferably about 0.01 to 0.30 mole, and may be practically about 0.01 to 0.25 mole, relative to 1 mole of the substrate.

The amount of the co-catalyst may be selected within a broad range of, for example, about 0.0001 mole (0.01 mole %) to 0.7 mole (70 mole %), preferably about 0.0001 mole to 0.5 mole, more preferably about 0.001 to 0.3 mole, andmaybe practically about 0.0005 to 0.1 mole (e.g., about 0.005 to 0.1 mole), relative to 1 mole of the substrate.

The ratio of the co-catalyst to the imide compound shown by the formula (1) may be selected within the range not interfering with the reaction rate or selectivity, for example, of about 0.001 to 10 mole of the co-catalyst, preferably about 0.005 to 5 mole, more preferably about 0.01 to 3 mole, andmay be practically about 0.01 to 5 mole, relative to 1 mole of the imide compound.

The amount of the nitrogen oxide may be selected depending upon the introduced amount of nitro group, within the range of, for example, about 1 mole or more (e.g., about 1 to 50 mole), preferably about 1.5 to 30 mole, and may be usually about 2 to 25 mole, relative to 1 mole of the substrate.

The amount of carbon monoxide may be selected within the range of, for example, about 1 mole or more (e.g., about 1 to 1000 mole), preferably excess mole, for example, about 1.5 to 100 mole (e.g., about 2 to 50 mole), more preferably about 2 to 30 mole (e.g., about 5 to 25 mole), relative to 1 mole of the substrate.

The amount of oxygen may be selected within the range of about 0.5 mole or more (e.g., about 0.5 to 100 mole), preferably about 0.5 to 30 mole, more preferably about 0.5 to 25 mole, relative to 1 mole of the substrate.

In a continuous reaction, when excess amount of carbon monoxide and oxygen are used, they can be used to supply to the reaction system continuously by, for example, circulating them.

The ratio of carbon monoxide (CO) to oxygen ($O_2$) may be selected within the wide range, as far as the amount of the each component is within the above range, for example, of $CO/O_2$=about 1/99 to 99.99/0.01 (mole %) [e.g., about 70/30 to 99/1 (mole %)]. Use of more amount of the carbon monoxide than that of oxygen is advantageous. The ratio of CO to $O_2$ may be usually selected within the range of $CO/O_2$=about 1/99 to 99/1 (mole %) [e.g., about 10/90 to 99/1 (mole %)], and may be preferably about 30/70 to 98/2 (mole %), more preferably about 50/50 to 95/5 (mole %), particularly about 60/40 to 90/10 (mole %).

The volume ratio of carbon monoxide to oxygen in a supply line may be selected within the range of, for example, $CO/O_2$=about 1/99 to 99.99/0.01 (volume %) [e.g., about 70/30 to 99/1 (volume %)], and may be usually about 1/99 to 99/1 (volume %), preferably about 30/70 to 98/2 (volume %), more preferably about 50/50 to 95/5 (volume %), specifically about 60/40 to 90/10.

Nitration Reaction and Carboxylation Reaction

The nitration reaction and/or the carboxylation reaction can be conducted in the presence or absence of a solvent. As the solvent, use can be made of a solvent inert to reaction, examples of which are organic acids (e.g., carboxylic acids such as acetic acid and propionic acid), nitriles (e.g., acetonitrile, propionitrile, benzonitrile), amides (e.g., formamide, dimethylformamide), alcohols (e.g., ethanol, propanol, butanol, t-butanol, t-amylalcohol), aliphatic hydrocarbons (e.g., hexane, octane), aromatic hydrocarbons (e.g., benzene), organic halogen compounds (e.g., halogenated hydrocarbons such as dichloromethane, chloroform, dichloroethane, dichlorobenzene, and trifluoromethylbenzene; halogen-substituted carboxylic acids such as chloroacetic acid and trifluoroacetic acid; halogen-substituted acid anhydrides such as chloroacetic anhydride; halogen-substituted esters such as methyl chloroacetate and ethyl chloroacetate), nitro compounds (e.g., nitromethane, nitrobenzene), esters (e.g., ethyl acetate), ethers (e.g., dimethyl ether), and mixed solvents of these. Among them, carboxylic acids (e.g., acetic acid, propionic acid), organic halogen compounds and nitrites are preferred as the solvent. A mixture of two or more solvents serves to enhance the yield and selectivity. As the solvent mixtures, there may be mentioned a mixed solvent comprising at least one solvent selected from nitriles and organic halogen compounds (e.g., a mixed solvent of a nitrile and an organic halogen compound, a mixed solvent of a nitrile and an organic acid), and the like. When the solvents are used in combination, the ratio for blending these solvents can be selected from a wide range. For instance, the ratio of a dominant primary solvent relative to the other solvent(s) ranges from about 1/99 to 99/1 (the former/the latter, by weight), preferably from about 5/95 to 95/5 (by weight), and more preferably about 10/90 to 90/10 (by weight) (e.g., 15/85 to 85/15 (by weight)).

In the present invention, the reactions can be smoothly conducted even in a comparatively mild or moderate condition. The reaction temperature may be suitably selected according to species of the reactions, species of the imide compounds or the substrates. For example, in the nitration reaction, the reaction temperature may be selected within the range of about 0 to 150° C., preferably about 25 to 125° C., more preferably about 30 to 100° C. The nitration reaction smoothly proceeds at a comparatively lower temperature such as within the range about 20 to 60° C. In the carboxylation reaction, the reaction temperature may be selected within the range of about 0 to 200° C., preferably about 10 to 150° C. (e.g., about 10 to 120° C.), more preferably about 10 to 100° C. (e.g., about 10 to 80° C.). The reaction can be conducted under ambient pressure or in a pressure (under load).

When a nitrogen oxide is used as a reactant, a reaction in the presence of oxygen sometimes provides a nitroalcohol or an alcohol. The nitroalcohol is included in the nitro compound of the present invention.

The process of the present invention is useful for nitrating and/or carboxylating a substrate to provide a nitro compound and/or carboxyl compound corresponding to the substrate, efficiently. In the process, the compound can be obtained with high conversion and selectivity even in a mild and moderate condition. To be specific, when a mixture of carbon monoxide and oxygen is employed as a reactant a carboxyl group can be directly introduced to a substrate, and a carboxyl compound having more carbon atoms than the substrate depending on the introduced amount of carboxyl groups. Thus, in the present invention, a substrate is contacted with carbon monoxide and oxygen in the presence of the catalyst to provide a carboxyl compound at fewer reaction steps.

The reaction may be conducted in any of a batch, semi-batch, or continuous system. After the completion of the reaction, the reaction product can be easily separated and purified by a conventional separation/purification method including such separation methods as filtration, concentration, distillation, extraction, crystallisation, recrystallisation, adsorption, column chromatography, and a combination of these separation methods.

Adamantane Derivative

In the adamantane derivative shown by the formulas (2) and (3), a protective group of a hydroxymethyl group (the moiety corresponding to hydroxyl group of hydroxymethyl group) is included, for instance, t-butyl group, a cycloalkyl group (e.g., cyclohexyl group), an aryl. group (e.g., 2,4-dinitrophenyl group), an aralkyl group (e.g., benzyl group, 2,6-dichlorobenzyl group, 3-bromobenzyl group, 2-nitrobenzyl group, 4-dimethylcarbamoylbenzyl group, a benzyl group which may have a substituent such as triphenylmethyl group), tetrahydropyranyl group, an acyl group [e.g., a suturated aliphatic acyl group [(e.g., a saturated $C_{2-6}$ aliphatic acyl group such as acetyl group, propionyl group, isopropionyl group, butyryl group, isobutyryl group, valeryl group, isovaleryl group, pyvaloyl group, preferably a $C_{2-4}$ saturated aliphatic acyl group), an aromatic acyl group (e.g., a $C_{7-13}$ aromatic acyl group such as benzoyl group, p-phenylbenzoyl, phthaloyl, naphtoyl), an alicyclic acyl group (a cycloalkyl-carbonyl group; such as cyclohexylcarbonyl)], an alkoxy carbonyl group such as a $C_{1-6}$ alkoxy-carbonyl group (e.g., methoxy carbonyl group, ethoxy carbonyl group, propyloxy carbonyl group, isopropyloxy carbonyl group, isobutyloxy carbonyl group, t-butyloxy carbonyl group), an alalkyloxy carbonyl group (e.g., benzyloxy carbonyl group, methoxybenzyloxy carbonyl group), a carbamoyl group, which may have a substituent such as a $C_{1-6}$ alkyl group and a $C_{6-14}$ aryl group, (e.g., carbamoyl group, methylcarbamoyl group, ethylcarbamoyl group, phenyl carbamoyl group), a dialkylphosphinotioyl group (e.g., dimethylphosphinotioyl group), a diarylphosphinotioyl group (e.g., diophenylphosphinotioyl group). A preferred protective group of hydroxymethyl group includes, for instance, an acyl group (specifically, a saturated $C_{2-6}$ aliphatic acyl group etc., more specifically, a saturated $C_{2-4}$ aliphatic acyl group etc.), a $C_{1-6}$ alkoxy-carbonyl group, a carbamoyl group which may have a substituent.

A protective group of amino group includes, for example, as illustrated in the paragraph of the protective group of the hydroxyl group, t-butyl group, an aralkyl group, a non-polymezable acyl group [such as a saturated aliphatic acyl group (e.g., a saturated $C_{2-6}$ aliphatic acyl group, especially, a saturated $C_{2-4}$ aliphatic acyl group), an aromatic acyl group (e.g., a $C_{7-13}$ aromatic acyl group), an alicyclic acyl group], an alkoxy carbonyl group (e.g., a $C_{1-6}$ alkoxy carbonyl group), an aralkyloxy carbonyl group, a dialkylphosphinotioyl group, a diarylphosphinotioyl group. A preferred protective group of amino group comprises, for instance, a non-polymerizable acyl group [such as a saturated $C_{2-6}$ aliphatic acyl group (specifically, a saturated $C_{2-4}$ aliphatic acyl group), a $C_{7-13}$ aromatic acyl group], an alkoxy carbonyl group (specifically, a $C_{1-6}$ alkoxy carbonyl group).

An N-substituted amino group includes, for example, a mono- or di-$C_{1-6}$ alkylamino group (e.g., methylamino group, ethylamino group, a propylamino group, dimethylamino group, diethylamino group), prefferably, a mono- or di-$C_{1-4}$ alkylamino group.

A protective group of a carboxyl group comprises, for instance, an alkoxy group such as a $C_{1-10}$ alkoxy group (e.g., methoxy group, ethoxy group, propoxy group, isopropoxy group, butoxy group, isobutoxy group, s-butoxy group, t-butoxy group, hexyloxy group), preferably, a $C_{1-6}$ alkoxy group, especially, a $C_{1-4}$ alkoxy group, a cycloalkyloxy group (e.g., cyclohexyloxy group), an aryloxy group (e.g., phenoxy group), an aralkyloxy group (e.g., benzyloxy group, diphenylmethyloxy group), a trialkylsilyloxy group (e.g., trimethylsilyloxy group), an amino group which may have a substituent [amino group; an N-substituted amino group, such as a mono- or di-$C_{1-6}$ alkyl amino group (e. g., methylamino group, dimethylamino group, ethylamino group, diethylamino group)], hydrazino group, an alkoxy carbonyl hydrazino group (e.g., t-butoxycarbonylhydrazino group), an aralkyloxycarbonylhydrazino group (e.g., benzyloxycarbonylhydrazino group). A preferred protective group of carboxyl group includes an alkoxy group (especially, a $C_{1-6}$ alkoxy group), an amino group which may have a substituent (e.g., an N-substituted amino group, especially, a mono- or di-$C_{1-6}$ alkylamino group).

An alkyl group comprises, for instance, a $C_{1-6}$ alkyl group, such as methyl, ethyl, propyl, isopropyl, butyl, isoutyl, s-butyl, t-butyl, hexyl, preferrably, a $C_{1-4}$alkyl group, more preferably, methyl group or ethyl group.

In the compound shown by the formula (3), a substituent of a carbamoyl group includes, for example, a $C_{1-6}$alkyl group such as methyl, ethyl, propyl, butyl, and isobutyl group and a $C_{6-14}$aryl group such as phenyl and naphthyl group. A substituted hydrooxycarbonylamino group includes, for example, a $C_{1-6}$alkoxy-carbonylamino group such as methoxycarbonylamino, ethoxycarbonylamino, propoxycarbonylamino, and butoxycarbonylamino group; a $C_{6-14}$aryloxy-carbonylamino group such as phenyloxycarbonylamino and naphtyloxycarbonylamino group; and a $C_{7-15}$aralkyloxy-carbonylamino group such as benzyloxycarbonylamino group.

Examples of a saturated aliphatic acylamino group include a saturated $C_{2-6}$aliphatic acylamino group such as acetylamino, propionylamino, isopropionylamino, butylylamino, isobutylylamino, valerylamino, isovalerylamino, and pivaloylamino group, and preferably a saturated $C_{2-4}$aliphatic acylamino group. An aromatic acylamino group includes, for example, an aromatic $C_{7-13}$acylamino such as benzoylamino and naphtoylamino group. A substituted oxycarbonyl group includes, for example, a $C_{1-6}$alkoxy-carbonyl group such as methoxycarbonyl, ethoxycarbonyl, propoxycarbonyl and butoxycarbonyl group; a $C_{6-14}$aryloxy-carbonyl group such as phenyloxycarbonyl and naphtyloxycarbonyl group; a $C_{7-15}$aralkyloxy-carbonyl group such as benzyloxycarbonyl group. An alkyl group as a substituent of an amino group includes, for example, a $C_{1-6}$alkyl group such as methyl, ethyl, propyl, butyl and isobutyl group.

Examples of a preferred $X^1$ include nitro group, amino group, a $C_{2-6}$acylamino group corresponding to an amino group protected by a $C_{2-6}$acyl group, a $C_{1-6}$alkoxycarbonylamino group corresponding to an amino group protected by a $C_{1-6}$alkoxy-carbonyl group, carboxyl group, a $C_{1-10}$-alkoxy-carbonyl group corresponding to a carboxyl group protected by a $C_{1-10}$loalkoxy group (especially, a $C_{1-6}$alkoxy-carbonyl group), a carbamoyl group, which may have a substituent, corresponding to a carboxyl group protected by an amino group which may have a substituent, hydroxymethyl group, isocyanato group. Examples of a preferred $X^2$ include amino group, a $C_{2-6}$acylamino group corresponding to an amino group protected by a $C_{2-6}$acyl group, a $C_{1-6}$alkoxy-carbonylamino group corresponding to an amino group protected by a $C_{1-6}$alkoxy-carbonyl group, hydroxymethyl group, isocyanato group, depending on species of $X^1$.

Examples of a preferred $X^3$ or $X^4$ include hydrogen atom, an alkyl group, nitro. group, amino group, a $C_{2-6}$acylamino group, a $C_{1-6}$alkoxy-carbonylamino group, carboxyl group, a $C_{1-10}$loalkoxy-carbonyl group (particularly a $C_{1-6}$alkoxy-carbonyl group), a carbamoyl group which may have a substituent, hydroxymethyl group and isocyanato group.

A preferred $X^5$ includes, for example, a carbamoyl group which may have a substituent, a $C_{1-6}$alkoxycarbonylamino group, a saturated aliphatic $C_{2-6}$acylamino group and an aromatic $C_{7-13}$acylamino group. A preferred $X^6$ includes, for example, carboxyl group, a $C_{1-10}$-alkoxycarbonyl group, amino group, a $C_{2-6}$acylamino group, a $C_{1-6}$alkoxycarbonylamino group and nitro group, depending on species of $X^5$.

A preferred $X^7$ or $X^8$ includes, for example, a substituent exemplified as the preferred $X^3$ or $X^4$.

When such novel adamantane derivatives have an acidic group or a basic group, they may form salts.

Among the compounds 'shown by the formula (2), as a nitro group-containing adamantane derivative, there may be exemplified 1-amino-3-nitroadamantane, 1-amino-3-methyl-5-nitroadamantane, 1-amino-3,5-dimethyl-7-nitroadamantane, 1-amino-3,5-dinitroadamantane, 1-methoxycarbonylamino-3-nitroadamantane, 1,3-bis (methoxycarbonylamino)-5-nitroadamnatane, 1-methoxycarbonylamino-3,5-dinitroadamantane, 1-ethoxycarbonylamino-3-nitroadamantane, 1-acetylamino-3-nitroadamantane, 1-acetylamino-3,5-dinitroadamantane, 1,3-bis(acetylamino)-5-nitroadamantane, 1-hydroxymethyl-3-nitroadamantane and 1-isocyanato-3-nitroadamantane.

As an adamantane derivative having an amino group or N-substituted amino group which may be protected by a protecting group, there may be mentioned, for example, 1-amino-3-isocyanatoadamantane, 1-amino-3-isocyanato-5-methyladamantane, 1-isocyanato-3-methoxycarbonylaminoadamantane, 1-isocyanato-3-(N-methylamino)adamantane and 1-acetylamino-3-isocyanatoadamantane.

Examples of an adamantane derivative having a carboxyl group which may be protected by a protecting group include 1-carboxy-3-hydroxymethyladamantane, 1,3-dicarboxy-5-hydroxymethyladamantane, 1-carboxy-3,5-bis (hydroxymethyl)adamantane, 1-carboxy-3-hydroxymethyl-5-methyladamantane, 1-hydroxymethyl-3-methoxycarbonyladamantane, 1-ethoxycarbonyl-3-hydroxymethyladamantane, 1-hydroxymethyl-3-(N,N-dimethylcarbamoyl)adamantane, 1-isocyanato-3-methoxycarbonyladamantane and 1-isocyanato-3-(N,N-dimethylcarbamoyl)adamantane.

An adamantane derivative having a hydroxymethyl group which may be protected by a protecting group includes, for example, 1-acetyloxymethyl-3-isocyanatoadamantane and 1-propionyloxymethyl-3-isocyanatoadamantane.

Among the adamantane derivatives shown by the formula (3), an adamantane derivative having a carbamoyl group which may have a substituent includes, for example, 1-carboxy-3-(N-methylcarbamoyl)adamantane, 1-carboxy-3-(N,N-dimethylcarbamoyl)adamantane, 1-carboxy-3-methyl-5-(N,N-dimethylcarbamoyl)adamantane, 1-methoxycarbonyl-3-(N,N-dimethylcarbamoyl) adamantane, 1-amino-3-(N,N-dimethylcarbamoyl) adamantane, 1-acetylamino-3-(N,N-dimethylcarbamoyl) adamantane, 1-methoxycarbonylamino-3-(N,N-dimethylcarbamoyl)adamantane and 1-(N,N-dimethylcarbamoyl)-3-nitroadamantane.

Examples of a nitro group-containing adamantane derivative include 1-methoxycarbonyl-3-nitroadamantane, 1,3-bis (methoxycarbonyl)-5-nitroadamantane, 1-methoxycarbonyl-3,5-dinitroadamantane, 1-methoxycarbonyl-3-methyl-5-nitroadamantane, 1-ethoxycarbonyl-3-nitroadamantane, 1-nitro-3-propoxycarbonyladamantane and 1-nitro-3-phenoxycarbonyladamantane.

A substituted hydroxycarbonylamino group-containing adamantane derivative includes, for example, 1-methoxycarbonyl-3-methoxycarbonylaminoadamantane, 1-methoxycarbonyl-3-methoxycarbonylamino-5-methyladamantane, 1-ethoxycarbonyl-3-ethoxycarbonylaminoadamantane, 1-hydroxymethyl-3-methoxycarbonylaminoadamantane, 1-amino-3-methoxycarbonylaminoadamantane, 1-amino-3-methoxycarbonylamino-5-methyladamantane, 1-acethylamino-3-methoxycarbonylaminoadamantane and 1-acetylamino-3-ethoxycarbonylaminoadamantane.

A saturated aliphatic or aromatic amino group-containing adamantane derivative includes, for example, 1-acetylamino-3-carboxyadamantane, 1,3-bis(acetylamino)-5-carboxyadamantane, 1-acetylamino-3,5-dicarboxyadamantane, 1-acetylamino-3-carboxy-5-methyladamantane, 1-benzoylamino-3-carboxyadamantane, 1-acetylamino-3-hydroxymethyladamantane, 1-acetylamino-3-aminoadamantane, 1,3-bis(acetylamino)-5-aminoadamantane, 1-acetylamino-3,5-diaminoadamantane, 1-acetylamino-3-(N,N-dimethylamino)adamantane and 1-acetylamino-3-(N-methylamino)adamantane.

The adamantane derivative shown by the formula (2) or (3) may have other substituents, for example, a halogen atom, an oxo group, a hydroxyalkyl group (e.g., hydroxy $C_{2-4}$alkyl groups such as 2-hydroxyethyl group), an acyl group (e.g., $C_{1-6}$acyl groups such as formyl, acetyl, propionyl, butyryl, isobutyryl, valeryl, isovaleryl and pivaloyl group), an alkoxycarbonyl group (e.g., $C_{1-6}$alkoxycarbonyl group such as methoxycarbonyl, ethoxy-carbonyl, propoxycarbonyl, isopropoxycarbonyl, butoxycarbonyl, isobutoxycarbonyl, t-butoxycarbonyl and hexyloxycarbonyl group) and cyano group.

Production of Adamantane Derivatives

The adamantane derivatives shown by the formulas (2) and (3) and an adamantane derivative having at least two substituents selected from the group consisting of a nitro group, an amino group or N-substituted amino group which may be protected by a protecting group, a carboxyl group which may be protected by a protecting group, a hydroxymethyl group which may be protected by a protecting group, and an isocyanato group, at a methine carbon atom of a bridgehead position of adanantane skelton can be obtained by the foll owing reaction step scheme (I) or (II), or by combining the reaction step scheme (I) and (II).

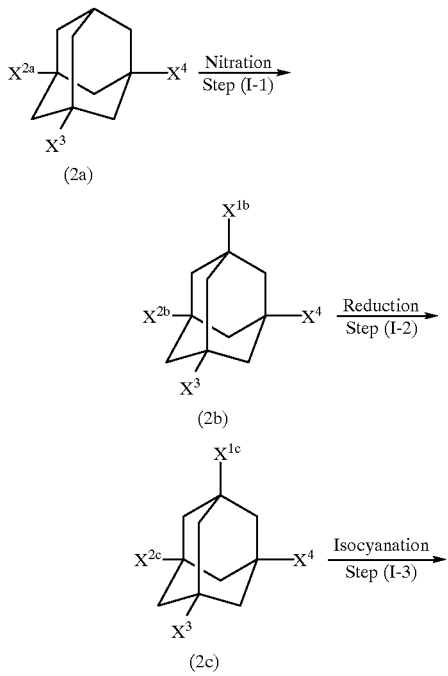

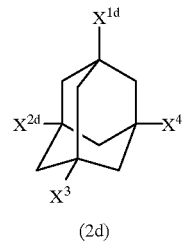

wherein $X^{1b}$ represents a nitro group; $X^{1c}$ represents an amino group; $X^{1d}$ represents an isocyanato group; $X^{2a}$, $X^{2b}$, $X^{2c}$ and $X^{2d}$ represent a hydrogen atom, a nitro group, an amino or N-substituted amino group which may be protected by a protecting group, a carboxyl group which may be protected by a protecting group, a hydroxymethyl group which may be protected by a protecting group, or an isocyanato group respectively; and $X^3$ and $X^4$ respectively have the same meanings as defined above).

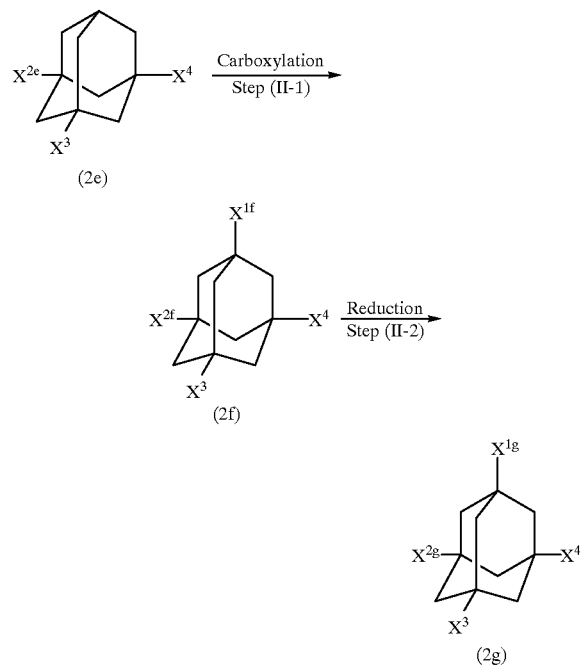

wherein $X^{1f}$ represents a carboxyl group; $X^{1g}$ represents a hydroxymethyl group; $X^{2e}$, $X^{2f}$ and $X^{2g}$ represents a hydrogen atom, a nitro group, an amino or N-substituted amino group which may be protected by a protecting group, a carboxyl group which may be protected by a protecting group, a hydroxymethyl group which may be protected by a protecting group, or an isocyanato group; and $X^3$ and $X^4$ each has the same meanings as defined above.)

The nitration (nitration reaction which derives compound (2b) from compound (2a)) of the step (I-1) in the reaction step scheme (I) may be carried out by the nitration method, i.e., the method of contacting a substrate with a nitrogen oxide at least, in the presence of the imide compound shown by the formula (1). A nitro group can be introduced to a methine carbon atom of a bridgehead position by the nitration. When $X^{2a}$ in the compound (2a) is hydrogen atom, $X^{2a}$ may be also converted into a nitro group according to reaction conditions. For example, nitration of an adamantane may give 1-nitroadamantane and/or 1,3-dinitroadamantane. Further, the nitration of 1-nitroadamantane, 1-carboxyadamantane and 1-hydroxyadamantane may give 1,3-dinitroadamantane, 1-carboxy-3-nitroadamantane and 1-hydroxy-3-nitroadamantane, respectively.

The reduction (reductive reaction which derives compound (2c) from compound (2b)) of the step (I-2) may be carried out by a conventional method such as catalytic hydrogenation process using hydrogen as a reducing agent and reduction process using a hydrogenation reducing agent.

In the catalytic hydrogenation, a simple substance of a metal such as platinum, palladium, nickel, cobalt, iron and copper, a compound containing such metal elements (e.g., platinum oxide, palladium black, palladium carbon and copper chromite) or the like may be used as a catalyst. The amount of the catalyst is practically about 0.02 to 1 mole relative to 1 mole of a substrate. Further, in a catalytic hydrogenation, the reaction temperature may be, for example, about −20 to 100° C. (e.g., about 0 to 90° C.). A hydrogen pressure is practically about 1 to 100 atm (e.g., about 1 to 50 atm).

In the reducing process using a hydrogenation reducing agent, the hydrogenation reducing agent to be used includes, for example, aluminium hydride, lithium aluminium hydride, lithium trialkoxyaluminium hydride, sodium boron hydride, diborane, bis-3-methyl-2-butylborane, ametal (e.g., zinc, tin, iron) acid, a sulfide and hydrazine. The reducing process using a hydrogenation reducing agent may be conducted also in the presence of a Lewis acid such as aluminium chloride anhydride and boron trifluoride. The amount of the hydrogenation reducing agent is usually about 1 mole or more (e.g., about 1 to 10 mole) relative to 1 mole of a substrate. In the reducing process using the hydrogenation reducing agent, a reaction temperature is practically about 0 to 200° C. (e.g., about 0 to 170° C.).

Incidentally, the reduction reaction (the catalytic hydrogenation and the process using the hydrogenation reducing agent) may be carried out in the presence of a solvent inert to the reduction reaction (e.g., an alcohol such as methanol and further a solvent exemplified in the nitration reaction such as a carboxylic acid, an ether, an ester and an amide). Moreover, when reduction reaction is conducted by the catalytic hydrogenation, an acid such as hydrochloric acid may be added to the reaction system in order to improve the catalytic activity.

The nitro group $X^{1b}$ of the compound (2b) is converted into an amino group by the reduction reaction. In the compound (2b), when $X^{2b}$ is a nitro group, the nitro group may be also converted into an amino group according to reaction conditions. For example, the reduction of 1-nitroadamantane may give 1-aminoadamantane, and the reduction of 1,3-dinitroadamantane may give 1-amino-3-nitroadamantane and/or 1,3-diaminoadamantane. Further, the each reduction of 1-carboxy-3-nitroadamantane and 1-hydroxymethyl-3-nitroadamantane may give 1-amino-3-carboxyadamantane and 1-amino-3-hydroxymethyladamantane respectively.

The isocyanation (reaction deriving compound (2d) from compound (2c)) of the step (I-3) may be carried out by a conventional method, for example, the method using phosgene. The reaction of the compound (2c) with phosgene may be conducted, for example, in the presence or absence of a solvent at a temperature of about −10 to 100° C. The amount of phosgene is, for example, about 0.8 to 10 mole and preferably about 1 to 2 mole relative to 1 mole of the compound (2c).

The amino group $X^{1c}$ of the compound (2c) may be converted into an isocyanato group by the reaction mentioned above. When $X^{2c}$ of the compound (2c) is an amino group, the amino group may be converted into an isocyanato group according to conditions. For example, the isocyanation of 1-aminoadamantane may give 1-isocyanatoadamantane. Further, each of 1-amino-3-nitroadamantane, 1.3-diaminoadamantane, 1-amino-3-carboxyadamantane and 1-amino-3-hydroxymethyladamantane may be subjected to isocyanation to give 1-isocyanato-3-nitroadamantane, 1,3-diisocynatoadamantane, 1-isocyanato-3-carboxyadamantane and 1-isocyanato-3-hydroxymethyladamantane respectively.

The carboxylation (reaction deriving compound (2f) from compound (2e)) of the step (II-1) in the reaction step scheme (II) may be carried out by the above-mentioned carboxylation, i.e., the process for contacting a substrate with at least carbon dioxide and oxygen in the presence of the imide compound shown by the formula (1). A carboxyl group can be introduced to a methine carbon atom at a bridgehead position of the compound (2e) by the carboxylation. When $X^{2e}$ of the compound (2e) is a hydrogen atom, $X^{2e}$ may be also converted to a carboxyl group according to reaction conditions. For example, an adamantane may be carboxylated to produce 1-carboxyadamantane and/or 1,3-dicarboxyadamantane as previously described. Further, the carboxylation of each 1-carboxyadamantane and 1-nitroadamantane may give 1,3-dicarboxyadamantane and 1-carboxy-3-nitroadamantane respectively.

The reduction (reaction introducing compound (2g) from compound (2f)) of the step (II-2) may be carried out by a conventional method such as catalytic hydrogenation using hydrogen as a reducing agent and a method using a hydrogenation reducing agent described for the step (I-2). In this step, a preferred hydrogenation reducing agent includes, for example, a sodium boron hydride-Lewis acid, aluminum hydride, lithium aluminum hydride, lithium trialkoxyaluminum hydride and diborane.

The reduction reaction may convert the carboxyl group $X^{1f}$ of the compound (2f) may be converted to a hydroxymethyl group. Moreover, when $X^{2f}$ of the compound (2f) is a carboxyl group, the carboxyl group may be also converted to a hydroxymethyl group according to reaction conditions. For example, the reduction of 1-carboxyadamantane gives 1-hydroxymethyladamantane, and the reduction of 1,3-dicarboxyadamantane gives 1-carboxy-3-hydroxymethyladamantane and/or 1,3-bis(hydroxymethyl)adamantane.

Incidentally, according to the species of substrates, a hydroxylmethyl group (a site corresponding to a hydroxyl group of the hydroxymethyl group), an amino group and a carboxyl group of the reaction component or the reaction product may be protected by the above protecting group before, after, or during the each step. The introduction and elimination of the protecting group for a hydroxymethyl group, an amino group and a carboxyl group may be carried out by a conventional method such as esterification, amidation, carbamation, carbonation, hydrolysis and hydrogenolysis, if necessary, using an acid, an alkali, an ion-exchange resin, a catalyst for hydrogenolysis or the like.

When an acyl group is.used as a protecting group for a hydroxylmethyl group or an amino group (acyloxymethyl group or acylamino group is formed), the hydroxymethyl group or the amino group of the substrate may be protected by allowing to act an acylating agent on the substrate. Examples of the acylating agent include $C_{2-6}$aliphatic monocarboxylic acids such as acetic acid, propionic acid, n-butyric acid, isobutyric acid, valeric acid and pivalic acid (preferably $C_{2-4}$carboxylic acids), and reactive derivatives thereof [e.g., acid anhydrides such as acetic anhydride and valeic anhydride, acid halides such as acid chloride (e.g., acetyl chloride, propionyl chloride and butyryl chloride)]. When an acid anhydride or an acid halide is used as an acylating agent, the acylation reaction is usually carried out in the presence of a base in order to capture the acid which is a by-product in the reaction. As the base, there may be exemplified an inorganic base (e.g., a hydroxide of an alkai metal such as sodium hydroxide; a hydroxide of alkaline earth metal such as barium hydroxide; carbonate of an alkaline metal such as sodium carbonate; a carbonate of an alkaline earth metal such as barium carbonate; a hydrogencarbonate of an alkaline metal such as sodium hydrogencarbonate); and an organic base (e.g., a tertiary amine such as triethylamine and N-methylpiperidine; a basic heterocyclic compound containing a nitrogen atom such as pyridine; an alkoxide of an alkali metal such as sodium methoxide and sodium ethoxide). The acylating agent may be used singly or in combination of two or more.

For example, 1-acetylamino-3-nitroadamantane can be obtained by acting acethyl chloride on 1-amino-3-nitroadamantane in the presence of the base.

When a substituted hydroxycarbonyl group is used as a protecting group for a hydroxymethyl group or an amino group, the hydroxyl group or the amino group may be protected by reacting a substrate with a halocarbonate to obtain a compound having a carbonate group or carbamate group. The reaction may be usually carried out in the presence of a base. As the base, the similar base to one exemplified above may be used.

When a carbamoyl group is used as a protecting group for a hydroxymethyl group, the hydroxymethyl group may be protected, for example, by reacting a substrate with an isocyanate compound, if necessary, in the presence of the base exemplified above to obtain a compound having a carbamoyloxy group.

Moreover, an adamantane derivative having N-substituted amino group may be produced, for example, by reacting a substrate with a hydrocarbon halide (e.g., aliphatic hydrocarbon halide such as iodomethane, iodoethane, iodobutane, bromomethane, bromoethane, bromobutane, chloromethane and chloroethane). The reaction may be conducted in the presence of a de-hydrogen halide agent (an agent for eliminating a hydrogen halide). As the de-hydrogen halide agent, a base, for example, the above exemplified may be practically used. The reaction may be conducted in solvent inert to the reaction. As such solvent, use may be made of exemplified solvents for the nitration reaction such as a hydrocarbon halide, an ether, an ester and an amide.

When a substituted hydroxyl group (e.g., an alkoxy group) protects a carboxyl group [(i.e., when a substituted hydroxycarbonyl group (an ester group)] is formed), the carboxyl group may be protected by reacting a carboxyl group-containing compound or derivative thereof (e.g., an acid halid such as an acid chloride) with an alcohol (e.g., methanol, ethanol) or reactive derivative thereof (e.g., lower alkyl ester), if necessary, in the presence of an acid (e.g., a mineral acid such as hydrochloric acid and sulfuric acid) or an base (e.g., the base exemplified above) to produce a compound having the corresponding ester group. The lower alkyl ester inclu des, for example, acetic acid-$C_{1-4}$alkyl ester such as methyl acetate and ethyl acetate or the corresponding propionate (e.g., methyl propionate, ethyl propionate). For example, 1-methoxycarbonyl-3-nitroadamantane may be obtained by reacting 1-carboxy-3-nitroadamantane with methanol in the presence of an acid, or by acting thionyl chloride on 1-carboxy-3-nitroadamantane followed by reacting with methanol in the presence of a base.

Moreover, when a carboxyl group is converted into a group having an amide bond with use of an amino group as a protecting group for the carboxyl group (i.e., when an N-substituted or unsubstituted carbamoyl group is formed), a condition of a conventional process for forming an amido bond may be applied. The process for forming an amido bond may be carried out, for example, by following methods:

(a) a method by a mixed acid anhydride, i.e., a method which comprises reacting a compound having a carboxyl group with an acid halide (e.g., acetyl chloride, propionyl chloride, acetyl bromide) to produce a mixed acid anhydride followed by reacting the given mixed acid anhydride with an amine compound;

(b) a method by an active ester, i.e., a method which comprises converting a substrate into an active ester thereof, such as p-nitrophenylester, an ester with N-hydroxysuccinimide, an ester with 1-hydroxybenzotriazol or the like followed by reacting the given ester with an amine compound;

(c) a method by a carbodiimide, i.e., a method which condenses an amine compound with a substrate in the presence of an activating agent such as dicyclohexylcarbodiimide and carbonyldlimidazol; or (d) a method which comprises converting a substrate into a carboxylic anhydride thereof by a dehydrator such as acetic anhydride followed by reacting the given carboxylic anhydride with an amine compound, or a method which comprises converting a substrate to an acid halide thereof followed by reacting the acid halide with an amine compound.

The amine compound used in the amide bond forming reaction includes, for example, ammonia or a derivative thereof (e.g., ammonium halide such as ammonium chloride), a primary amine, a secondary amine, hydrazine or a derivative thereof (e.g., alkoxycarbonylhydrazine such as t-butoxycarbonylhydrazine, alkoxycarbonylhydrazine such as benzyloxycarbonylhydrazine).

For example, the reaction of an acid halide with an amine compound may be carried out in a suitable solvent, in the presence of an basic compound. As the basic compound, use may be made of a basic compound exemplified for the reaction of the compound (Ia) having an amino group or the compound (1d) with a hydrocarbon halide and the like.

Moreover, as the solvent, an organic solvent (e.g., an ether, an ester, an amide) exemplified for the nitration reaction may be employed.

Furthermore, the compound having a carbamoyl group may be obtained by reacting a compound having an ester group (e.g., an alkoxycarbonyl group, an aryloxycarbonyl group, an aralkyloxycarbonyl group) as a protected carboxyl group with the amine compound in the presence of a catalyst comprising a metal compound.

Examples of the metal compound used in the reaction (the amidation reaction) include a conventional catalyst for transesterification (including a catalyst for transferring an ester to an amide), for example, a transition metal compound such as a compound comprising Group 3B element of the Periodic Table of Elements (e.g., aluminum compound such as $AlCl_3$), a compound comprising Group 4A element of the Periodic Table of Elements (e.g., titanium compound such as $TiCl_4$), a compound comprising Group 3A element (e.g., samarium compound such as $SmI_2$) of the Periodic Table of Elements.

The amount of the catalyst may be liberally selected within a broad range, for example, about 0.1 mole % to 1 equivalent, preferably about 0.5 to 50 mole %, and more preferably about 1 to 25 mole % (e.g., about 5 to 20 mole %) relative to a compound having an ester group.

The ratio of the amine compound to the ester group-containing compound is, for example, about 0.5 to 5 mole, preferably about 0.8 mole or more (e.g., about 0.8 to 5 mole), and specifically about 1 mole or more (e.g., about 1 to 3 mole, in particular about 1 to 1.5 mole) of ammonia or the like relative to 1 equivalent of the ester group-containing compound.

The amidation reaction may be carried out in the presence or absence of a solvent inert to the reaction. As the reaction solvent, there may be exemplified an aliphatic hydrocarbon, an alicyclic hydrocarbon, an aromatic hydrocarbon, a ketone, an ether, a non-protonic polar solvent and a mixture thereof. The reaction temperature may be selected within the range of, for example, about 0 to 150° C., and preferably about 25 to 120° C.

The adamantane derivative shown by the formula (2) and (3) of the present invention can be concretely produced as follows.

For example, among compounds shown by the formula (2), a compound having a nitro group and an amino group which may have a protecting group or a substituent can be produced through the steps (I-1) and (I-2). A compound having a nitro group and an isocyanato group can be produced through the steps (I-1), (I-2) and (I-3). A compound having a nitro group and a hydroxymethyl group which may be protected by a protecting group may be obtained through the steps (I-1), (II-1) and (II-2).

A compound having an amino group which may have a protective group or a substituent, and an isocyanato group may be produced through the steps (I-1), (I-2) and (I-3).

A compound having a carboxyl group, which may be protected by protective group, and a hydroxymethyl group which may be protected by a protecting group may be obtained, for example, through the step (II-1) and (II-2). A compound having a carboxyl group which may be protected by a protecting group, and an isocyanato group may be obtained through the steps (I-1), (I-2), (I-3) and (II-1).

A compound having a hydroxylmethyl group which may be protected by a protecting group, and an isocyanato group may be produced through the steps (I-1), (I-2), (I-3), (II-1) and (II-2).

Among the compounds shown by the formula (3), a compound having a carbamoyl group which may have a substituent, and a carboxyl group may be obtained through the step (II-1) and the step of introducing an amino group to a carboxyl group (the amide group-forming step). A compound having a carbamoyl group which may have a substituent, and a substituted hydroxycarbonyl group may be obtained through the step (II-1), the step for introducing an amino group to a carboxyl group and the step for introducing a substituted hydroxyl group to another carboxyl group (the ester group-forming step). A compound having a carbamoyl group which may have a substituent, and an amino group which may have a protecting group or a substituent may be obtained through the steps (I-1), (I-2), (II-1) and the step of introducing an amino group to the carboxyl group. A compound having a carbamoyl group which may have a substituent, and a nitro group may be obtained through the steps (I-1), (II-1) and the step of introducing an amino group to the carboxyl group.

A compound having a nitro group and a substituted hydroxycarbonyl group may be produced through the steps (I-1), (II-1), and the step of introducing a substituted hydroxyl group to the carboxyl group. A compound having a substituted hydroxycarbonylamino group and a substituted hydroxycarbonyl group may be obtained through the steps (I-1), (I-2), (II-1) and the step of introducing the substituted hydroxycarbonyl group to an amino group (the carbamate group-forming step) and the step of introducing a substituted hydroxyl group to the carboxy group. A compound having a substituted hydroxycarbonylamino group and, a hydroxyl group may be protected by a protecting group through the steps (I-1), (I-2), (II-1), (II-2), and the step of introducing an amino group to the substituted hydroxycarbonyl group. A compound having a substituted hydroxycarbonylamino group and an amino group which may be protected by a protecting group may be obtained through the steps (I-1), (I-2), (I-3), and the step of introducing an substituted hydroxycarbonyl group to the amino group. A compound having a saturated aliphatic or aromatic acylamino group and a carboxylg roup may be obtained through the steps (I-1), (I-2), (II-1), and the step of introducing an acyl group to an amino group. A compound having a saturated aliphatic or aromatic acylamino group and a hydroxylmethyl group which may be protected by a protecting groupmaybeobtainedthroughthesteps (I-1), (I-2), (II-1), (II-2), and the step of introducing an acyl group to an amino group. A compound having a saturated aliphatic or aromatic acylamino group and an amino group which may be protected by an alkyl group may be obtained through the steps (I-1), (I-2), and the step of introducing an acyl group to an amino group. The introduction of an amino group or a substituted hydroxyl group to a carboxyl group, introduction of a substituted hydroxycarbonyl group to an amino group, and introduction of an acyl group to an amino group may be carried out by the above method for introducing a protecting group.

Further, the diaminoadamantane derivative (compound (2j)) having at least two groups of amino groups or N-substituted amino groups, which may be protected by a protecting group, at bridgehead position of adamantane skeleton may be obtained by nitrating the compound (compound (2h)) in which $X^{2a}$ of the compound (2a) is a hydrogen atom or a nitro group according to the step (I-1) to form a dinitro body (compound (2i)) in which $X^{1b}$ and $X^{2b}$ of the compound (2b) are nitro groups, and then reducing it according to the step (I-2) to convert into a diamino body in which $X^{1c}$ and $X^{2c}$ of the compound (2c) are an amino groups and, if necessary, introducing a protecting group or a substituent to the amino group. In the method, since the diamino body is directly formed in the form of not salt but free, the alternation or denaturation, decomposition or decrease of recover efficiency, each occuring when salt of a diamino body becomes free may be avoid. Therefore, the diamino adamantane derivative may be efficiently produced with high yield.

INDUSTRIAL APPLICABILITY

In the method of the present invention, a substrate may be directly nitrated and/or carboxylated efficiently even in a mild or moderate condition since an imide compound shown by the formula (1) is combined with at least one reacting agent selected from (i) a nitrogen oxide and (ii) a mixture of carbon monoxide and oxygen. Moreover, to a substrate, at least one functional group selected from a nitro group and a carboxyl group can be introduced to produce a nitro compound and/or carboxy compound with high conversion and selectivity even in the mild or moderate condition.

Moreover, nitrogen oxide, which causes environmental pollution, is efficiently utilized to form a nitro compound may be produced with high conversion and selectivity. Further, a carboxy compound having more carbon atoms than that of a substrate may be efficiently produced by a simple operation through fewer steps.

Further, in the present invention, a novel adamantane derivative useful for a high functional material may be provided. A diamino body of adamantane can be produced in high yield.

EXAMPLES

The following examples are intended to describe this invention in further detail and should by no means be interpreted as defining the scope of the invention. Incidentally, infrared absorption spectra were measured after purifying the reaction product by column chromatography.

Example 1

Into a flask, 1 mmole of adamantane, 0.05 mmole of N-hydroxyphthalimide and 5 ml of acetic acid were added to mix and then the flask was equipped with a gas bag (about 1L) of nitrogen monoxide NO. The mixture was reacted for 8 hours at 100° C. with stirring. The reaction products were analyzed by gas chromatography, and, as a result, The conversion of adamantane was 95%, and nitroadamantane (yield 30%), adamantanol (yield 17%) and acetyloxyadamantane (yield 33%) were formed.

Examples 2 to 5

Into a flask, 1 mmole of adamantane, 0.05 mmole of N-hydroxyphthalimide and 5 ml of the solvent represented in Table 1 were added to mix, and then the flask was equipped with a gas bag (about 1L) of nitrogen monoxide NO. The mixture was heated to 100° C. with stirring. After the period of time shown in Table 1, the reaction products were analyzed by gas chromatography, and, as a result, nitro compounds were formed with conversions and yields represented in Table 1.

TABLE 1

| Sol-vents | Times (hr) | Conver-sions(%) | Com. 1 | Com. 2 | Com. 3 | Com. 4 | Com. 5 |
|---|---|---|---|---|---|---|---|
| | | | Yields(%) | | | | |
| Ex.2 BzCN | 5 | 76 | 16 | 0 | 19 | 9 | 8 |
| Ex.3 AcOH | 10 | 95 | 11 | 22 | 20 | 10 | 10 |

TABLE 1-continued

| Sol-vents | Times (hr) | Conver-sions(%) | Com. 1 | Com. 2 | Com. 3 | Com. 4 | Com. 5 |
|---|---|---|---|---|---|---|---|
| | | | Yields(%) | | | | |
| Ex.4 AcOH | 16 | 99 | 4 | 17 | 30 | 15 | 18 |
| Ex.5 DCE | 16 | 64 | 19 | 0 | 18 | 6 | 4 |

BzCN: benzonitorile
AcOH: acetic acid
DCE: dichloroethane
Com. 1: adamantanol
Com. 2: acetyloxyadamantane
Com. 3: nitroadmantane
Com. 4: adamantanediol
Com. 5: nitroadamantano

Examples 6 to 8

Into a flask, 1 mmole of adamantane, 0.05 mmole of N-hydroxyphthalimide and 5 ml of the solvent shown in Table 2 were added to mix and the flask was purged by nitrogen monoxide NO (about 1L) and oxygen $O_2$ (about 1L). The mixture was reacted for 10 hours at the temperatures shown in Table 2, with stirring. Reaction products were analyzed by gas chromatography, and, as a result, nitro compounds were formed with yields represented in Table 2.

Meanings of the symbols shown in Table 2 are as follows.

TABLE 2

| Solvents | Temperatures (° C.) | Conver-sions(%) | Com.1 | Com.2 | Com.3 | Com.4 | Com.5 |
|---|---|---|---|---|---|---|---|
| | | | Yields(%) | | | | |
| Ex.6 AcOH | 100 | 99 | 4 | 11 | 43 | 10 | 21 |
| Ex.7 AcCN + DCE | 60 | 89 | 5 | 10 | 50 | 6 | 11 |
| Ex.8 BzCN + AcOH | 100 | 99 | 1 | 1 | 79 | 1 | 3 |

AcOH: acetic acid
AcCN: acetonitrile
BzCN: benzonitorile
DCE: dichloroethane
Com. 1: adamantanol
Com. 2: acetyloxyadamantane
Com. 3: nitroadmantane
Com. 4: adamantanediol
Com. 5: nitroadamantanol

Example 9

An eggplant type flask with side arm was dipped in iced water and reduced pressure. Into the flask, not only nitrogen monoxide and oxygen was introduced from a gasbag (1L). Theflask was filledwith reddish-browngas, and then the reddish-brown gas sedimented to form blue liquid which comprised $N_2O_3$ as a main component was formed with sedimentation of. The introductions of the nitrogen monoxide and oxygen were repeated to produce about 1.5 ml of the blue liquid. The blue liquid was frozen with use of liquid nitrogen.

1.8 g (0.024 mole based on $N_2O_3$ basis) of the frozen blue liquid, 1 mmole of adamantane, 0.05 mmole of N-hydroxyphthalimide and 5 ml of acetic acid were mixed, and then the mixture was reacted for 10 hours at 100° C. with stirring. The reaction products were analyzed by gas chromatography, and, as a result, nitroadamantane (yield 81%) was formed with conversion of 99%.

Example 10

The nitration reaction was effected in the same manner as Example 9 except that 1.8 g (0.024 mole based on $N_2O_3$) of the frozen blue liquid, 1 mole of adamantane, 0. 05 mmole of N-hydroxyphthalimide and 5 ml acetic acid were mixed and then the mixture was reacted for 16 hours at 25° C. with stirring. As a result, nitroadamantane was formed. The conversion of adamantane was 83% and the yield of the nitroadamantane was 72%.

Example 11

Into a flask, 1 mmole of adamantane, 0.1 mmole of N-hydroxyphthalimide, 2 ml of nitrogen dioxide ($N_2O$), 6 ml of benzonitrile (6 ml) and 1.2 ml of acetic acid were added and stirred for 12 hours at 60° C. in an atmosphere of nitrogen monoxide (NO). The reaction products were analyzed by gas chromatography, and, as a result, the conversion of adamantane was 98%, nitroadamantane (yield 68%), adamantanol (yield 6%) and acetyloxyadamantane (yield 4%) were formed.

Example 12

The reaction was effected in the same manner as Example 11 except for stirring in an atmosphere of oxygen instead of the atmosphere of nitrogen oxide (NO)). Ni-troadamantane (yield 78%), adamantanol (yield 1%), acetyloxyadamantane (yield 1%) andadamantanone (yield 3%) were formed. The conversion of adamantane was 98%.

Example 13

The reaction was effected in the same manner as Example 11 except for stirring in an atmosphere of an inert gas (argon) instead of the atmosphere of nitrogen oxide (NO)). Nitroadamantane (yield 76%), adamantanol (yield 1%), acetyloxyadamantane (yield 6%) andadamantanon (yield 6%) were formed. The conversion of adamantane was 97%.

Example 14

Into a flask, 1 mmole of ethylbenzene, 0.05 mmole of N-hydroxyphthalimide and 5 ml of acetic acid were added to mix and the flask was equipped with a gas bag (about 1L)of nitrogen monoxide NO. The mixture was reacted for 8 hours at 100° C. with stirring. The reaction products were analyzed by gas chromatography, and, as a result, the conversion of ethylbenzene was 85%, and 1-nitroethylbenzene (yield 14%), 1-hydroxyethylbenzene (yield 18%) and 1-acetyloxyethylbenzene (yield 30%) were formed.

Example 15

Into a flask, 1 mmole of adamantane, 0.1 mmole of N-hydroxyphthalimide and 6 ml of acetic acid were added to mix. The flask was purged by nitrogen monoxide NO (about 1L) and oxygen $O^2$ (about 1L), and then the mixture was reacted for 20 hours at 110° C. with stirring. The reaction products were analyzed by gas chromatography, and, as a result, the conversion of adamantane was 90%, and 1-nitroadamantane (yield 64%) and 1,3-dinitroadamantane (yield 12%) were formed.

Example 16

The operation was effected in the same manner as Example 15 except for using 1-nitroadamantane instead of adamantane. 1,3-dinitroadamantane(yield 80%)wasformed. The conversion of 1-nitroadamantane was 90%.

Incidentally, when the reaction time was 6 hours, the conversion of 1-nitroadamantane was 33% and the yield of 1,3-dinitroadamantane was 27%.

Pale yellow solid; Mass spectral data $[M]^+$: 226; IR($cm^{-1}$): 1560, 1360, 750.

Example 17

Into a flask, 1 mmole of adamantane, 0.1 mmole of N-hydroxyphthalimide, 6 ml of benzonitrile and 1 ml of acetic acid were added to mix and the flask was equipped with a gas bag (about 1L) of nitrogen monoxide NO. The mixture was reacted for 20 hours at 100° C. with stirring. The reaction products were analyzed by gas chromatography, and, as a result, the conversion of adamantane was 92%, and 1-benzoylaminoadamantane (yield 65%), 1-adamantanol (yield 7%), 1-nitroadamantane (yield 6%), 1-acetyloxyadamantane (yield 2%) and 2-adamantanone (yield 2%) were formed.

Example 18

Into a flask, 2 mmole of toluene, 0.2 mmole of N-hydroxyphthalimide, 6 ml of 1,2-dichloroethane and 1.2 ml of acetonitrile were added to mix. The mixture was reacted for 12 hours at 60° C. with stirring in an atmosphere of nitrogen dioxide $NO_2$. The reaction products were analyzed by gas chromatography, and, as a result, the conversion of toluene was 47%, and 2-nitrotoluene (yield 18%), nitromethylbenzene (yield 9%) and 4-nitrotoluene (yield 9%) were formed.

Example 19

The operation was effected in the same manner as Example 18 except for conducting the reaction after purged by nitrogen monoxide NO and oxygen $O_2$ (molar ratio 1:1) to reaction system instead of nitrogen dioxide $NO_2$. 2-nitrotoluene (yield 20%), nitromethylbenzene (yield 7%) and 4-nitrotoluene (yield 3%) were formed. The conversion of toluene was 52%.

Example 20

The operation was effected in the same manner as Example 19 except for using ethylbenzene instead of toluene. The conversion of ethylbenzene was 100%, and 1-nitroethylbenzene (yield 13%), 2-nitro-1-ethylbenzene (yield 21%) and 4-nitro-1-ethylbenzene (yield 18%) were formed.

Example 21

The operation was effected in the same manner as Example 20 except for using nitrogen dioxide $NO_2$ and oxygen $O_2$ (molar ratio 1:1) instead of nitrogen monoxide NO and oxygen $O_2$ and reacting for 8 hours. The conversion of ethylbenzene was 100%, and 1-nitroethylbenzene (yield 15%), o-nitroethylbenzene (yield 19%) and m-nitroethylbenzene (yield 13%) were formed.

Example 22

The operation was effected in the same manner as Example 20 except for using nitrogen dioxide $NO_2$ and nitrogen monoxide NO (molar ratio 1:1) instead of nitrogen monoxide NO and oxygen $O_2$ and reacting for 8 hours. The conversion of ethylbenzene was 91%, and 1-nitroethylbenzene (yield 11%), o-nitroethylbenzene (yield 3%) and acetophenone (yield 14%) were formed.

Example 23

Into a flask, 1 mmole of adamantane, 0.05 mmole of N-hydroxyphthalimide, 15 mmole of nitrogen dioxide (NO$_2$) and 3 ml of acetonitrile were added and stirred for 5 hours at 60° C. in an atmosphere of oxygen. The reaction products were analyzed by gas chromatography, and, as a result, the conversion of adamantane was 97%, and nitroadamantane (yield 65%), dinitroadamantane (yield 1%), adamantanol (yield 1%), acetyloxyadamantane (yield 3%) and adamantanone (yield 2%) were formed.

Example 24

The reaction was effected in the same manner as Example 23 except that the amount of N-hydroxyphthalimide was 0.1 mmole and the reaction time was 3 hours. The conversion of adamantane was 98%, and nitroadamantne (yield 69%), adamantanol (yield 1%), acetyloxyadamantane (yield 2%) and adamantanone (yield 2%) were formed.

Example 25

Into a flask, 1 mmole of adamantane, 0.05 mmole of N-hydroxyphthalimide, 15 mmole of nitrogen dioxide (NO$_2$) and 3 ml of trifluoromethylbenzene were added and stirred for 5 hours at 60° C. in an atmosphere of oxygen. The reaction products were analyzed by gas chromatography, and, as a result, the conversion of adamantane was 79%, and nitroadamantane (yield 57%), adamantanol (yield 6%) and adamantanone (yield 4%) were formed.

Example 26

The reaction was effected in the same manner as Example 25 except that the amount of N-hydroxyphthalimide was 0.1 mmole. The conversion of adamantane was 96%, and nitroadamantane (yield 66%), adamantanol (yield 4%) and adamantanone (yield 5%) were formed.

Example 27

Into a flask, 1 mmole of adamantane, 0.05 mmole of N-hydroxyphthalimide, 15 mmole of nitrogen dioxide (NO$_2$), 1 ml of acetonitrile and 2 ml of trifluoromethylbenzene were added and stirred for 5 hours at 60° C. in an atmosphere of oxygen. The reaction products were analyzed by gas chromatography, and, as a result, the conversion of adamantane was 90%, and nitroadamantane (yield 73%), adamantanol (yield 2%), acetyloxyadamantane (yield 1%) and adamantanone (yield 3%) were formed.

Example 28

The reaction was effected in the same manner as Example 27 except that the amount of N-hydroxyphthalimide was 0.1 mmole. The conversion of adamantane was 95%, and nitroadamantane (yield 76%), adamantanol (yield 1%), acetyloxyadamantane (yield 1%) and adamantanone (yield 3%) were formed.

Example 29

The reaction was effected in the same manner as Example 28 except that the amount of acetonitrile was 0.5 ml and that the amount of trifluoromethylbenzene was 2.5 ml. The conversion of adamantane was 89%, and nitroadamantane (yield 70%), adamantanol (yield 1%), acetyloxyadamantane (yield 1%) and adamantanone (yield 4%) were formed.

Example 30

Into a flask, 1 mmole of adamantane, 0.05 mmole of N-hydroxyphthalimide, 15 mmole of nitrogen dioxide (NO$_2$) and 3 ml of dichloroethane were added and stirred for 5 hours at 60° C. in an atmosphere of oxygen. The reaction products were analyzed by gas chromatography, and, as a result, the conversion of adamantane was 97%, and nitroadamantane (yield 57%), adamantanol (yield 12%) and adamantanone (yield 4%) were formed.

Example 31

Into a flask, 1 mmole of adamantane, 0.1 mmole of N-hydroxyphthalimide, 15 mmole of nitrogen dioxide (NO$_2$) and 3 ml of acetic acid were added and stirred for 5 hours at 60° C. in an atmosphere of oxygen. The reaction products were analyzed by gas chromatography, and, as a result, the conversion of adamantane was. 96%, and nitroadamantane (yield 75%), adamantanol (yield 1%), acetyloxyadamantane (yield 5%) and adamantanone (yield 4%) were formed.

Example 32

Into a flask, 1 mmole of adamantane, 0.1 mmole of N-hydroxyphthalimide, 0.0005 mmole of acetylacetonatomanganese(II) Mn(AA)$_2$ and 5 ml of acetic acid were added to mix and the flask was equipped with a gas bag (about 1L) of nitrogen monoxide NO. The mixture was reacted for 8 hours at 100° C. with stirring. The reaction products were analyzed by gas chromatography, and, as a result, the conversion of adamantane was 95%, and nitroadamantane (yield 75%) was formed.

Example 33

The reaction was effected in the same manner as Example 32 except for using acetylacetonatomanganese (III) Mn(AA)$_3$ instead of Mn(AA)$_2$. The conversion of adamantane was 72%, and nitroadamantane (yield 66%) was formed.

Example 34

The reaction was effected in the same manner as Example 32 except for using molybdic acid H$_2$MoO$_4$ instead of Mn(AA)$_2$. The conversion of adamantane was 62%, and nitroadamantane (yield 57%) was formed.

Example 35

The reaction was effected in the same manner as Example 32 except for using acetylacetonatoiron(III) Fe(AA)$_3$ instead of Mn(AA)$_2$. The conversion of adamantane was 56%, and nitroadamantane (yield 50%) was formed.

Example 36

The reaction was effected in the same manner as Example 32 except for using managanese acetate Mn(Oac)$_2$ instead of Mn(AA)$_2$. The conversion of adamantane was 77%, and nitroadamantane (yield 72%) was formed.

Example 37

The reaction was effected in the same manner as Example 32 except for using 0.0001 mmole of acetylacetonatocobalt (II) Co(AA)$_2$ instead of Mn(AA)$_2$. The conversion of adamantane was 82%, and nitroadamantane (yield 75%) was formed.

Example 38

The reaction was effected in the same manner as Example 32 except for using acetylacetonatonickel(II) Ni(AA)$_2$ instead of Mn(AA)$_2$. The conversion of adamantane was 54%, and nitroadamantane (yield 49%) was formed.

Example 39

The reaction was effected in the same manner as Example 32 except for using acetylacetonatochromium(III) Cr(AA)$_3$ instead of Mn(AA)$_2$. The conversion of adamantane was 72%, and nitroadamantane (yield 66%) was formed.

Example 40

The reaction was effected in the same manner as Example 32 except for using acetylacetonatocopper(II) Cu(AA)$_2$ instead of Mn(AA)$_2$. The conversion of adamantane was 52%, and nitroadamantane (yield 46%) were formed.

Example 41

The reaction was effected in the same manner as Example 32 except for using acetylacetonatocopper(III) Cu(AA)$_3$ instead of Mn(AA)$_2$. the conversion of adamantane was 48%, and nitroadamantane (yield 42%) were formed.

Example 42

Into a flask, 1 mmole of 1-carboxyadamantane, 0.1 mmole of N-hydroxyphthalimide and 6 ml of acetic acid were added to mix. The mixture was purged by nitrogen monoxide NO (about 1L) and oxygen O$_2$ (about 1L), and then reacted for 20 hours at 110° C. with stirring. The reaction products were analyzed by gas chromatography, and, as a result, the conversion of 1-carboxyadamantane was 90%, and 1-carboxy-3-nitroadamantane (yield 80%) was formed.

Pale yellow solid; Mass spectral data [M]$^+$: 225; IR(cm$^-$$_1$): 2990, 1620, 1560;

Example 43

The reaction was effected in the same manner as Example 42 except for using 1-hydroxymethyladamantane instead of 1-carboxyadamantane. The conversion of 1-hydroxymethyladamantane was 90%, and 1-hydroxymethyl-3-nitroadamantane (yield 70%) was formed.

Pale yellow solid; Mass spectral data [M]$^+$: 211; IR(cm$^-$$_1$): 3350, 1550, 1370;

Example 44

To acetic acid, the mixture of 10 mmole of adamantane, 1 mmole of N-hyd roxyphthalimide (NHPI) and 0.005 mmole of acetylaceto natocobalt(II) Co(AA)$_2$ was charged and the container was equipped with a gas bag charged with mixed gas (mixed gas comprised 2L of carbon monoxide and 0.5L of oxygen; pressure: 5 kg/cm$^2$). The mixture was stirred f or 6 hours at 60° C. The products in the reaction mixture were analyzed by gas chromatography, and, as a result, the conversion of adamantane was 76%, and 1-carbpxyadamantane (yield 70%) was formed.

Example 45

The reaction was effected in the same manner as Example 44 except for using acetylacetonatomanganese(II) Mn(AA)$_2$ instead of Co(AA)$_2$. The conversion of adamantane was 68%, and 1-carboxyadamantane (yield 62%) were formed.

Example 46

The reaction was effected in the same manner as Example 44 except for using acetonitrile instead of acetic acid. The conversion of adamantane was 73%, and 1-carboxyadamantane (yield 69%) were formed.

Example 47

The reaction was effected in the same manner as Example 44 except for using dichloroethane instead of acetic acid. The conversion of adamantane was 81%, and 1-carboxyadamantane (yield 75%) were formed.

Example 48

The reaction was effected in the same manner as Example 44 except that the reaction temperature was 80° C. The conversion of adamantane was 87%, and 1-carboxyadamantane (yield 81%) was formed.

Example 49

The reaction was effected in the same manner as Example 44 except for using 1-methyladamantane instead of adamantane. The conversion of 1-methyladamantane was 71%, and 1-carboxy-3-methyladamantane (yield 66%) was formed.

Example 50

The reaction was effected in the same manner as Example 44 except for using toluene instead of adamantane. The conversion of toluene was 67%, and phenyl acetate (yield 61%) were formed.

Example 51

The reaction was effected in the same manner as Example 44 except for using ethylbenzene instead of adamantane and that the pressure of the mixed gas was 10 kg/cm$^2$. The conversion of ethylbenzene was 71%, and 1-phenylpropionic acid (yield 56%) was formed.

Example 52

The reaction was effected in the same manner as Example 44 except for using fluorene instead of adamantane and that the pressure of the mixed gas was 10 kg/cm$^2$. The conversion of fluorene was 73%, and 9-carboxyfluorene (yield 69%) were formed.

Example 53

To the solvent mixture of 3 ml of acetic acid and 3 ml of 1,2-dichloroethane, a mixture of 10 mmole of tetrahydrodicyclopentadiene, 3 mmole of N-hydroxyphthalimide(NHPI) and 0.05 mmole of acetylaceto-natocobalt(II) Co(AA)$_2$ was charged. The reaction mixture was stirred for 15 hours at 85° C. in an atmosphere of mixed gas of carbon monoxide and air (partial pressure of carbon monoxide: 45 kg/cm$^2$, partial pressure of air: 1 kg/cm$^2$). The products in the reaction mixture were analyzed by gas chromatography, and, as a result, the conversion of tetrahydrodicyclopentadiene was 68%, and 1-carboxytetrahydrodicyclopentadiene (yield 38%) was formed.

Example 54

The reaction was effected in the same manner as Example 53 except for using acetylacetonatomanganese(II) Mn(AA)$_2$ instead of Co(AA)$_2$. The conversion of tetrahydrodicyclopentadiene was 66%, and 1-carboxytetrahydrodicyclopentadiene (yield 38%) were formed.

Example 55

The reaction was effected in the same manner as Example 44 except for using acetylacetonatomanganese(III) Mn(AA)$_3$ instead of Co(AA)$_2$. The conversion of adamantane was 66%, and 1-carboxyadamantane (yield 62%) was formed.

Example 56

The reaction was effected in the same manner as Example 44 except for using molybdic acid H$_2$MoO$_4$ instead of Co(AA)$_2$. The conversion of adamantane was 58%, and 1-carboxyadamantane (yield 52%) was formed.

Example 57

The reaction was effected in the same manner as Example 44 except for using acetylacetonatoiron(III) Fe(AA)$_3$ instead of Co(AA)$_2$. The conversion of adamantane was 52%, and 1-carboxyadamantane (yield 50%) was formed.

Example 58

The reaction was effected in the same manner as Example 44 except for using manganese acetate Mn(OAc)$_2$ instead of Co(AA)$_2$. The conversion of adamantane was 71%, and 1-carboxyadamantane (yield 66%) was formed.

Example 59

The reaction was effected in the same manner as Example 44 except for using 0.005 mmole of acetylacetonatomanganese(II) Mn(AA)$_2$ and 0.001 mmole of Co(AA)$_2$ instead of Co(AA)$_2$. The conversion of adamantane was 74%, and 1-carboxyadamantane (yield 71%) was formed.

Example 60

The reaction was effected in the same manner as Example 44 except for using acetylacetonatonickel(III) Ni(AA)$_2$ instead of Co(AA)$_2$. The conversion of adamantane was 51%, and 1-carboxyadamantane (yield 47%) was formed.

Example 61

The reaction was effected in the same manner as Example 44 except for using acetylacetonatochromium(III) Cr(AA)$_3$ instead of Co(AA)$_2$. The conversion of adamantane was 62%, and 1-carboxyadamantane (yield 60%) was formed.

Example 62

The reaction was effected in the same manner as Example 44 except for using acetylacetonatocopper(II) Cu(AA)$_2$ instead of Co(AA)$_2$. The conversion of adamantane was 47%, and 1-carboxyadamantane (yield 41%) was formed.

Example 63

The reaction was effected in the same manner as Example 44 except for using acetylacetonatocopper(III) Cu(AA)$_3$ instead of Co(AA)$_2$. The conversion of adamantane was 48%, and 1-carboxyadamantane (yield 43%) was formed.

Example 64

The reaction was effected in the same manner as Example 44 except for using 1-carboxyadamantane instead of adamantane. The conversion of 1-carboxyadamantane was 80%, and 1,3-dicarboxyadamantane (yield 70%) was formed.

White solid; Mass spectral data [M]$^+$: 224; IR(cm$^{-1}$): 3010, 1630, 1140.

Comparative Example 1

The stirring was carried out in the same manner as Example 44 without use of NHPI. No carboxyadamantane was detected.

Comparative Example 2

The stirring was carried out in the same manner as Example 44 without use of oxygen. No carboxyadamantane was detected.

Example 65

To an autoclave, 10 mmole of 1,3-dinitroadamantane obtained by the method of Example 16, 5% Pd-C (10 mole % of Pd relative to a substrate), 1 ml of dilute hydrochloric acid and 10 ml of methanol were charged. The mixture was stirred for 2 hours at 80° C. in an atmosphere of hydrogen at 30 atm. As a result, the conversion of 1,3-dinitroadamantane was 99%, and 1,3-diaminoadamantane (yield 95%) was formed.

Pale yellow solid; Mass spectral data [M]$^+$: 166; IR(cm$^{-1}$): 3310, 1520, 870.

Example 66

The reaction was effected in the same manner as Example 65 except for using Raney nickel (5 mole % of Ni relative to a substrate) instead of 5% Pd-C and that reacting for 4 hours. The conversion of 1,3-dinitroadamantane was 99%, and 1-amino-3-nitroadamantane (yield 80%) was formed.

Pale yellow solid; Mass spectral data [M]$^+$: 166; IR(cm$^{-1}$): 3310, 1520, 870.

Example 67

In an atmosphere of nitrogen, 11 mmole of acetyl chloride and 12 mmole of triethylamine were dissolved in 2 ml of tetrahydrofurane (THF). To the resultant solution, 10 mmole of 1-amino-3-nitroadamantane obtained by the method of Example 66 and 10 ml of N,N-dimethylformamide (DMF) were added. The mixture was stirred for 3 hours at 40° C. As a result, the conversion of 1-amino-3-nitroadamantane was 99%, and 1-acetylamino-3-nitroadamantane (yield 95%) was formed.

Pale yellow liquid; Mass spectral data [M]$^+$: 238; IR(cm$^{-1}$): 1680, 1550, 680.

Example 68

In an atmosphere of nitrogen, 10 mmole of 1-carboxy-3-nitroadamantane obtained by the method of Example 42 was dissolved in 10ml of DMF. To the mixture, 15 mmole of acetyl chloride was added dropwise over 30 minutes. The mixture was heated to begin to reflux around the conclusion of the addition. After refluxing for 2 hours, the mixture was cooled, 20 mmole of triethylamine was added, and then 11 mmole of methanol was added dropwise over 30 minutes while retaining the temperature of the mixture at 10° C. or less followed by stirring for more 2 hours. As a result, the conversion of 1-carboxy-3-nitroadamantane was 99%, and 1-methoxycarbonyl-3-nitroadamantane (yield 95%) was formed.

Pale yellow solid; Mass spectral data [M]$^+$: 239; IR(cm$^{-1}$): 1730, 1560, 1120.

Example 69

In an atmosphere of nitrogen, 10 mmole of 1-carboxy-3-nitroadamantane obtained by the method of Example 43 was dissolved in 10 ml of DMF. To the mixture, 15 mmole of acetyl chloride was added dropwise over 30 minutes. The mixture was heated to begin to reflux around the conclusion of the addition. After refluxing for 2 hours, the mixture was cooled, and 25 mmole of dimethylamine was added dropwise over 30 minutes while retaining the temperature of the mixture at 10° C. or less followed by stirring for more 2 hours. As a result, the conversion of 1-carboxy-3-nitroadamantane was 99%, and 1-(N,N-dimethylcarbamoyl)-3-nitroadamantane (yield 95%) was formed.

Pale yellow solid; Mass spectral data $[M]^+$: 252; IR($cm^-_1$): 1660, 1560, 690.

Example 70

The operation was effected in the same manner as Example 57 except for using 1-carboxy-3-nitroadamantane obtained by the method of Example 42 instead of 1,3-dinitroadmantane. The conversion of 1-carboxy-3-nitroadamantane was 80%, and 1-amino-3-carboxyadamantane (yield 70%) was formed.

Pale yellow solid; Mass spectral data $[M]^+$: 195; IR($cm^-_1$): 3370, 3000, 1670, 1620.

Example 71

The operation was effected in the same manner as Example 67 except for using 1-amino-3-carboxyadamantane obtained by the method of Example 70 instead of 1-amino-3-nitroadmantane. The conversion of 1-amino-3-carboxyadamantane was 99%, and 1-acetylamino-3-carboxyadamantane (yield 95%) was formed.

Pale yellow liquid; Mass spectral data $[M]^+$: 234; IR($cm^-_1$): 3360, 1670, 1640.

Example 72

The operation was effected in the same manner as Example 68 except for using 1,3-dicarboxyadamantane obtained by the method of Example 64 instead of 1-carboxy-3-nitroadmantane. The conversion of 1,3-dicarboxyadamantane was 90%, and 1-carboxy-3-methoxycarbonyladamantane (yield 80%) was formed.

White solid; Mass spectral data $[M]^+$: 238; IR($cm^{-1}$): 3030, 1670, 1630.

Example 73

In an atmosphere of nitrogen, 15 mmole of lithium aluminum hydride was suspended in 15 ml of THF. To the mixture, 10 mmole of 1,3-dicarboxyadamantane obtained by the method of example 64 was added slowly while retaining the temperature of the mixture at 10° C. or less with use of an ice bath. After warming to the room temperature, the mixture was refluxed for 16 hours. As a result, The conversion of 1,3-dicarboxyadamantane was 90%, and 1-carboxy-3-hydroxymethyladamantane (yield 80%) was formed.

White solid; Mass spectral data $[M]^+$: 210; IR($cm^{-1}$): 3350, 3000, 1650.

Example 74

The operation was effected in the same manner as Example 69 except for using 1,3-dicarboxyadamantane obtained by the method of Example 64 instead of 1-carboxy-3-nitroadmantane. The conversion of 1,3-dicarboxyadamantane was 90%, and 1-carboxy-3-(N,N-dimethylcarbamoyl)adamantane (yield 80%) was formed.

Pale yellow solid; Mass spectral data $[M]^+$: 251; IR($cm^-_1$): 3010, 1670, 1630.

Example 75

The operation was effected in the same manner as Example 67 except for using 1, 3-diaminoadamantane obtained by the method of Example 65 instead of 1-amino-3-nitroadmantane. The conversion of 1,3-diaminoadamantane was 90%, and 1-acetylamino-3-aminoadamantane (yield 80%) was formed.

Pale yellow liquid; Mass spectral data $[M]^+$: 208; IR($cm^-_1$): 3350, 1660, 760.

Example 76

The operation was effected in the same manner as Example 68 except for using 1-amino-3-carboxyadamantane obtained by the method of Example 70 instead of 1-carboxy-3-nitroadmantane. The conversion of 1-amino-3-carboxyadamantane was 99%, and 1-amino-3-methoxycarbonyladamantane (yield 95%) was formed.

Pale yellow solid; Mass spectral data $[M]^+$: 209; IR($cm^-_1$): 3330, 1630, 770.

Example 77

The operation was effected in the same manner as Example 66 except for using 1-hydroxymethyl-3-nitroadamantane obtained by the method of Example 43 instead of 1,3-dinitroadmantane. The conversion of 1-hydroxymethyl-3-nitroadamantane was 99%, and 1-amino-3-hydroxymethyladamantane (yield 95%) was formed.

Pale yellow solid; Mass spectral data $[M]^+$: 181; IR($cm^-_1$): 3300, 1160, 760.

Example 78

The operation was effected in the same manner as Example 66 except for using 1-(N,N-dimethylcarbamoyl)-3-nitroadamantane obtained by the method of Example 69 instead of 1,3-dinitroadmantane. The conversion of 1-(N,N-dimethylcarbamoyl)-3-nitroadamantane was 90%, and 1-amino-3-(N,N-dimethylcarbamoyl) adamantane (yield 80%) was formed.

Pale yellow solid; Mass spectral data $[M]^+$: 222; IR($cm^-_1$): 3310, 1670, 1140.

Example 79

The operation was effected in the same manner as Example 68 except for using 1-acetylamino-3-carboxyadamantane obtained by the method of Example 71 instead of 1-carboxy-3-nitroadmantane. 1-acetylamino-3-methoxycarbonyladamantane (yield 80%) was formed. The conversion of 1-acetylamino-3-carboxyadamantane was 90%.

Pale yellow liquid; Mass spectral data $[M]^+$: 251; IR($cm^-_1$): 3300, 1660, 1620.

Example 80

The operation was effected in the same manner as Example 67 except for using 1-amino-3-hydroxymethyladamantane obtained by the method of Example 77 instead of 1-amino-3-nitroadmantane. The conversion of 1-amino-3-hydroxymethyladamantane was 90%, and 1-acetylamino-3-hydroxymethyladamantane (yield 80%) was formed.

Pale yellow liquid; Mass spectral data $[M]^+$: 223; IR($cm^-_1$): 3310, 1650, 1160.

Example 81

The opeartion was effected in the same manner as Example 67 except for using 1-amino-3-(N,N- dimethylcarbamoyl)adamantane obtained by the method of Example 78 instead of 1-amino-3-nitroadmantane. The conversion of 1-amino-3-(N,N-dimethylcarbamoyl)adamantane was 90%, and 1-acetylamino-3-(N,N-dimethylcarbamoyl)adamantane (yield 80%) was formed.

Pale yellow solid; Mass spectral data $[M]^+$: 264; IR($cm^{-1}$): 3300, 1670, 1650, 740.

Example 82

The operation was effected in the same manner as Example 68 except for using 1-hydroxymethyl-3-carboxyadamantane obtained by the method of Example 73 instead of 1-carboxy-3-nitroadmantane. The conversion of 1-hydroxymethyl-3-carboxyadamantane was 90%, and 1-hydroxymethyl-3-methoxycarbonyladamantane (yield 80%) was formed.

White solid; Mass spectral data $[M]^+$: 224; IR($cm^{-1}$): 3310, 1620, 1430.

Example 83

In an atmosphere of nitrogen, 22 mmole of acetyl chloride and 24 mmole of triethylamine were dissolved in 2 ml of tetrahydrofurane (THF). To the resultant solution, 10 ml of solution containing 10 mmole of 1,3-diaminoadamantane obtained by the method of Example 65 in N,N-dimethylformamide (DMF) was added and then stirred for 3 hours at 40° C. As a result, the conversion of 1,3-diaminoadamantane was 99%, and 1,3-bis(acetylamino)adamantane (yield 95%) was formed.

Pale yellow liquid; Mass spectral data $[M]^+$: 250; IR($cm^{-1}$): 3330, 1660, 1240.

Example 84

In an atmosphere of nitrogen, 10 mmole of 1,3-dicarboxyadamantane obtained by the method of Example 64 was dissolved in 10 ml of DMF. To the mixture, 30 mmole of thionyl chloride was added dropwise over 30 minutes and the mixture was heated to begin to reflux around the conclusion of addition. After refluxing for 2 hours, the mixture was cooled. To the mixture, 40 mmole of triethylamine was added followed by 22 mmole of methanol over 30 minutes while retaining the temperature of the mixture at 10° C. or less, and then stirred for more 2 hours. As a result, the conversion of 1, 3-dicarboxyadamantane was 99%, and 1,3-bis(methoxycarbonyl)adamantane (yield 95%) was formed.

White solid; Mass spectral data $[M]^+$: 252; IR($cm^{-1}$): 1620, 1240, 1030.

Example 85

In an atmosphere of nitrogen, 30 mmole of lithium aluminum hydride was suspended in 15 ml of THF. To the mixture, 10 mmole of 1,3-dicarboxyadamantane obtained by the method of Example 64 was added slowly while retaining the temperature of the mixture at 10° C. or less with use of a ice bath. After heating to the room temperature, the mixture was refluxed for 16 hours. As a result, the conversion of 1,3-dicarboxyadamantane was 99%, and 1,3-bis(hydroxymethyl)adamantane (yield 95%) was formed.

White solid; Mass spectral data $[M]^+$: 196; IR($cm^{-1}$): 3310, 1490, 720.

Example 86

In an atmosphere of nitrogen, 10 mmole of 1,3-dicarboxyadamantane obtained by the method of Example 64 was dissolved in 10 ml of DMF. To the mixture, 30 mmole of thionyl chloride was added dropwise over 30 minutes and the mixture was heated to begin to reflux around the conclusion of addition. After refluxing for 2 hours, the mixture was cooled. To the mixture, 50 mmole of dimethylamine was added dropwise over 30 minutes while retaining the temperature of the mixture at 10° C. or less, and then stirred for more 2 hours. As a result, the conversion of 1,3-dicarboxyadamantane was 99%, and 1,3-bis(N,N-dimethylcarbamoyl)adamantane (yield 95%) was formed.

Pale yellow solid; Mass spectral data $[M]^+$: 278; IR($cm^{-1}$): 1670, 1420, 1170.

Example 87

1 mmole of 1,3-bis(methozxycarbonyl)adamantane obtained by the method of Example 84 was dissolved in 30 ml of THF. To the mixture, 0.5 mmole of dimethylamine and 0.1 mmole of aluminum chloride anhydride $AlCl_3$ was added and reacted for 6 hours at 80° C. As a result, The conversion of 1,3-bis(methoxycarbonyl)adamantane was 90%, and 1-methoxycarbonyl-3-(N,N-dimethylcarbamoyl)adamantane (yield 80%) was formed.

Pale yellow solid; Mass spectral data $[M]^+$: 265; IR($cm^{-1}$): 1670, 1630, 1170.

Example 88

In an atmosphere of nitrogen, 10 mmole of 1-carboxy-3-hydroxymethyladamantane obtained by the method of Example 73 was dissolved in 10 ml of DMF. To the mixture, 15 mmole of N,N'-carbodiimidazol in the form of powder was added in one portion. After stirring for 1 hour at the room temperature, 15 mmole of dimethylamine and 15 mmole of diazabicycloundecene were added. The mixture was heated to 100° C. and stirred for 8 hours. As a result, the conversion of 1-carboxy-3-hydroxymethyladamantane was 99%, and 1-hydroxymethyl-3-(N,N-dimethylcarbamoyl)adamantane (yield 95%) was formed.

Pale yellow liquid; Mass spectral data $[M]^+$: 237; IR($cm^{-1}$): 3310, 1660, 1220.

Example 89

10 mmole of 1-amino-3-nitroadamantane obtained by the method of Example 66 was dissolved in toluene (100 ml). To the resultant solution, 12 mmole of phosgene was added at the room temperature and stirred for 6 hours. As a result, The conversion of 1-amino-3-nitroadamantane was 99%, and 1-isocyanato-3-nitroadamantane (yield 90%) was formed.

Pale yellow liquid; Mass spectral data $[M]^+$: 222; IR($cm^{-1}$): 2200, 1560, 1330, 750.

Example 90

The operation was effected in the same manner as Example 89 except for using 1-aminoadamantane instead of 1-amino-3-nitroadmantane. The conversion of 1-aminoadamantane was 99%, and 1-isocyanatoadamantane (yield 90%) was formed.

Pale yellow liquid; Mass spectral data $[M]^+$: 177; IR($cm^{-1}$): 3300, 2180, 1270.

Example 91

The operation was effected in the same manner as Example 80 except for using 1,3-diaminoadamantane obtained by the method of Example 65 instead of 1-amino-3-nitroadmantane. The conversion of 1,3-diaminoadamantane was 90%, and 1-isocyanatoademantane (yield 80t) was formed.

Pale yellow liquid; Mass spectral data $[M]^+$: 192; IR($cm^{-1}$): 3310, 2270, 1520, 870.

Example 92

The operation was effected in the same manner as Example 89 except for using 1-amino-3-(N,N- dimethylcarbamoyl)adamantane obtained by the method of Example 78 instead of 1-amino-3-nitroadmantane. The conversion of 1-amino-3-(N,N-dimethylcarbamoyl)adamantane was 95%, and 1-isocyanato-3-(N,N-dimethylcarbamoyl) adamantane (yield 85%) was formed.

Pale yellow liquid; Mass spectral data $[M]^+$: 248; IR($cm^{-1}$): 2200, 1640, 1310, 750.

Example 93

The operation was effected in the same manner as Example 89 except for using 1-amino-3-methoxycarbonyladamantane obtained by the method of Example 78 instead of 1-amino-3-nitroadmantane. The conversion of 1-amino-3-methoxycarbonyladamantane was 95%, and 1-isocyanato-3-methoxycarbonyladamantane (yield 85%) was formed.

Pale yellow liquid; Mass spectral data $[M]^+$: 235; IR($cm^{-1}$): 2220, 1640, 1330, 770.

Example 94

To the mixture of 10 mmole of adamantane, 1 mmole of NHPI, 0.005 mmole of Co(AA)$_2$ and 25 ml of acetic acid, nitrogen monoxide (NO), carbon monoxide (CO) and oxygen (O$_2$) were introduced in the ratio of NO:CO:O$_2$ (molar ratio)=10:15:1 at the pressure of 26 kg/cm$^2$ and then stirred for 6 hours at 100° C. The reaction products were analyzed by gas chromatography and gas-mass spectrum apparatus, and as a result, 1,3,5-trinitroadamantane (yield 5%), 1-carboxy-3,5-dinitroadamantane (yield 5%), 1,3-dicarboxy-5-nitroadamantane (yield 1%) and 1,3,5-tricarboxyadamantane (yield 1%) were formed.

What is claimed is:

1. A process which comprises contacting a substrate with at least one reactant selected from (i) a nitrogen oxide and (ii) a mixture of carbon monoxide and oxygen at least in the presence of a catalyst to introduce at least one functional group selected from a nitro group and a carboxyl group to the substrate, wherein the catalyst comprises an imide compound shown by the following formula (1):

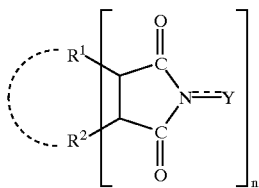

(1)

wherein R$^1$ and R$^2$ may be same or different from each other, and represent a hydrogen atom, a halogen atom, an alkyl group, an aryl group, a cycloalkyl group, a hydroxyl group, an alkoxy group, a carboxyl group, an alkoxycarbonyl group, and an acyl group, and R$^1$ and R$^2$ may bond together to form a double bond, or an aromatic or non-aromatic ring; Y represents an oxygen atom or a hydroxyl group; and n denotes an integer of 1 to 3.

2. A process according to claim 1, said substrate is a member selected from (a) a compound having a methyl group or a methylene group at an adjacent site of an unsaturated bond, (b) a homo- or hetero cyclic compound having a methylene group, (c) a compound having a methine carbon atom, (d) a compound having a methyl group or a methylene group at an adjacent site of an aromatic ring and (e) a compound having a methylene group at an adjacent site of a carbonyl group.

3. A process according to claim 1, said substrate is a compound having a methine carbon atom or a compound having a methyl or methylene group at a benzyl site of the compound.

4. A process according to claim 1, wherein said nitrogen oxide is shown by the formula:

$N_xO_y$ wherein x denotes an integer of 1 or 2 and y denotes an integer of 1 to 6.

5. A process according to claim 1, wherein said nitrogen oxide comprises at least one nitrogen compound selected from $N_2O_3$ and $NO_2$ as a main component.

6. A process according to claim 1, wherein not less than 1 mole of carbon monoxide and not less than 0.5 mole of oxygen relative to 1 mole of said substrate are employed.

7. A process according to claim 1, a ratio of carbon monoxide to oxygen is carbon monoxide/oxygen=about 1/99 to 99.99/0.01 (mole ratio).

8. A process according to claim 1 wherein the catalyst comprises said imide compound shown by the formula (1) and a co-catalyst.

9. A process for producing a compound having at least one functional group selected from a nitro group and a carboxyl group, which comprises, at least in the presence of a catalyst, contacting a substrate with at least one reactant selected from (i) a nitrogen oxide and (ii) a mixture of carbon monoxide and oxygen, wherein the catalyst comprises an imide compound shown by the following formula (1):

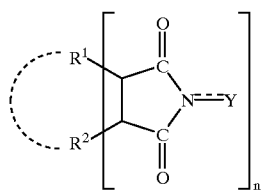

(1)

wherein R$^1$ and R$^2$ may be the same or different from each other, and represent a hydrogen atom, a halogen atom, an alkyl group, an aryl group, a cycloalkyl group, a hydroxyl group, an alkoxy group, a carboxyl group, an alkoxycarbonyl group, and an acyl group, and R$^1$ and R$^2$ may bond together to form a double bond, or an aromatic or non-aromatic ring; Y represents an oxygen atom or a hydroxyl group; and n denotes an integer of 1 to 3.

10. A process according to claim 9 wherein the catalyst comprises said imide compound shown by the formula (1) and a co-catalyst.

11. An adamantane derivative shown by the following formula (2):

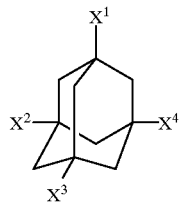

(2)

wherein X$^1$ represents a nitro group, an amino group or N-substituted amino group which may be protected by a protective group, a carboxyl group which may be protected by a protective group, or a hydroxymethyl group which may be protected by a protective group; and X$^3$ and X$^4$ may be the same or different from each other, and represents a hydrogen atom, an alkyl group, a nitro group, an amino group or N-substituted amino group which may be protected by a protective group, a carboxyl group which may be protected by a protective group, a hydroxymethyl group which may be protected by a protective group or an isocyanato group;

(i) when $X^1$ is a nitro group, $X^2$ represents N-amino group which may be protected by a protective group, a hydroxymethyl group which may be protected by a protective group, or an isocyanato group;

(ii) when $X^1$ is an amino group or N-substituted amino group which may be protected by a protective group, $X^2$ represents an isocyanato group;

(iii) when $X^1$ is a carboxyl group which may be protected by a protective group, $X^2$ represents a hydroxymethyl group which may be protected by a protective group, or an isocyanato group; and (iv) when $X^1$ is a hydroxymethyl group which may be protected by a protective group, $X^2$ represents an isocyanato group;

or a salt thereof.

12. An adamantane derivative shown by the following formula (3):

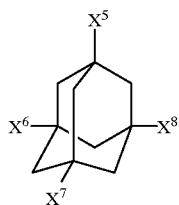

(3)

wherein $X^5$ represents a carbamoyl group which may have a substituent, a nitro group, a substituted hydroxycarbonylamino group, or a saturated aliphatic acylamino group or aromatic acylamino group; $X^7$ and $X8$ are the same or different from each other, and represent a hydrogen atom, an alkyl group, a nitro group, an amino or N-substituted amino group which may be protected by a protective group, a carboxyl group which may be protected by a protective group, a hydroxymethyl group which may be protected by a protective group, or an isocyanato group;

(i) when $X^5$ is a carbamoyl group which may have a substituent, $X^6$ represents a carboxyl group, a substituted hydroxycarbonyl group, or a nitro group;

(ii) when $X^5$ is a nitro group, $X^6$ represents a substituted hydroxycarbonyl group;

(iii) when $X^5$ is a substituted hydroxycarbonylamino group, $X^6$ represents a substituted hydroxycarbonyl group, a hydroxymethyl group which may be protected by a protective group, or an amino group which may be protected by a protective group; and (iv) when $X^5$ is a saturated aliphatic acylamino group or aromatic acylamino group, $X^6$ represents an amino group which may be substituted by an alkyl group;

or a salt thereof.

13. A process for producing a diaminoadamantane derivative shown by the following formula (2j):

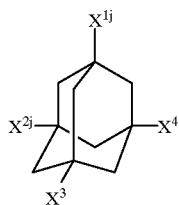

(2j)

wherein $X^{1j}$ and $X^{2j}$ represent an amino group or N-substituted amino group which may be protected by a protective group; and $X^3$ and $X^4$ are the same or different from each other, and represent a hydrogen atom, an alkyl group, a nitro group, an amino group or N-substituted amino group which may be protected by a protective group, a carboxyl group which may be protected by a protective group, a hydroxymethyl group which may be protected by a protective group, or an isocyanato group;

or a salt thereof, which comprises the steps of contacting a compound shown by the following formula (2h):

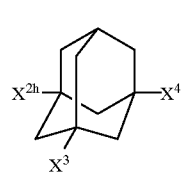

(2h)

wherein $X^{2h}$ represents a hydrogen atom or a nitro group; $X^3$ and $X^4$ are have the same meanings as defined above; with a nitrogen oxide, in the presence of an imide compound shown by the following formula (1):

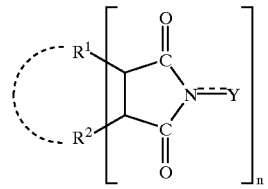

(1)

wherein $R^1$ and $R^2$ are the same or different from each other and represents a hydrogen atom, a halogen atom, an alkyl group, an aryl group, a cycloalkyl group, a hydroxyl group, an alkoxy group, a carboxyl group, an alkoxycarbonyl group, and an acyl group; $R^1$ and $R^2$ may bond together to form a double bond, or an aromatic or nonaromatic ring; Y represents an oxygen atom or a hydroxyl group; and n denotes an integer of 1 to 3, to produce a dinitroadamantane derivative shown by the following formula (2i):

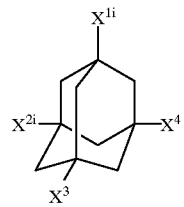

(2i)

wherein $X^{1i}$ and $X^{2i}$ each represents a nitro group; and $X^3$ and $X^4$ have the same meanings as defined above; and reducing said dinitroadamantane derivative shown by the formula (2i) to produce a corresponding diamino compound.

* * * * *